US008895546B2

(12) United States Patent
Cartt et al.

(10) Patent No.: US 8,895,546 B2
(45) Date of Patent: Nov. 25, 2014

(54) ADMINISTRATION OF BENZODIAZEPINE COMPOSITIONS

(75) Inventors: Steve Cartt, San Carlos, CA (US); David Medeiros, South San Francisco, CA (US); Garry Thomas Gwozdz, Jim Thorpe, PA (US); Andrew Loxley, Philadelphia, PA (US); Mark Mitchnick, East Hampton, NY (US); David Hale, San Diego, CA (US); Edward T. Maggio, San Diego, CA (US)

(73) Assignee: Hale Biopharma Ventures, LLC, Encinitas, CA (US)

( * ) Notice: Subject to any disclaimer, the term of this patent is extended or adjusted under 35 U.S.C. 154(b) by 0 days.

(21) Appl. No.: 13/495,942

(22) Filed: Jun. 13, 2012

(65) Prior Publication Data

US 2013/0065886 A1 Mar. 14, 2013

Related U.S. Application Data

(63) Continuation-in-part of application No. 12/413,439, filed on Mar. 27, 2009.

(60) Provisional application No. 61/497,017, filed on Jun. 14, 2011, provisional application No. 61/570,110, filed on Dec. 13, 2011.

(51) Int. Cl.
*A61K 31/55* (2006.01)
*A61K 9/00* (2006.01)
*A61K 31/355* (2006.01)
*A61K 31/5513* (2006.01)
*A61K 45/06* (2006.01)

(52) U.S. Cl.
CPC ............. *A61K 31/355* (2013.01); *A61K 9/0043* (2013.01); *A61K 31/5513* (2013.01); *A61K 9/008* (2013.01); *A61K 45/06* (2013.01)
USPC ......................................................... 514/221

(58) Field of Classification Search
USPC ......................................................... 514/221
See application file for complete search history.

(56) References Cited

U.S. PATENT DOCUMENTS

| | | |
|---|---|---|
| 3,102,116 A | 8/1963 | Chase et al. |
| 3,109,843 A | 11/1963 | Reeder et al. |
| 3,136,815 A | 6/1964 | Reeder et al. |
| 3,243,427 A | 3/1966 | Reeder et al. |
| 3,296,249 A | 1/1967 | Bell |
| 3,299,053 A | 1/1967 | Archer et al. |
| 3,340,253 A | 9/1967 | Reeder et al. |
| 3,371,085 A | 2/1968 | Reeder et al. |
| 3,374,225 A | 3/1968 | Reeder et al. |
| 3,547,828 A | 12/1970 | Mansfield et al. |
| 3,567,710 A | 3/1971 | Fryer et al. |
| 3,609,145 A | 9/1971 | Moffett |
| 3,722,371 A | 3/1973 | Boyle |
| 3,849,341 A | 11/1974 | Lambeiti |
| 3,987,052 A | 10/1976 | Hester, Jr. |
| 4,280,957 A | 7/1981 | Walser et al. |
| 4,397,951 A | 8/1983 | Taki et al. |
| 4,608,278 A | 8/1986 | Frank et al. |
| 4,748,158 A | 5/1988 | Biermann et al. |
| 4,826,689 A | 5/1989 | Violanto et al. |
| 4,868,289 A | 9/1989 | Magnusson et al. |
| 4,921,838 A | 5/1990 | Catsimpoolas et al. |
| 4,973,465 A | 11/1990 | Baurain et al. |
| 4,997,454 A | 3/1991 | Violanto et al. |
| 5,091,188 A | 2/1992 | Haynes |
| 5,100,591 A | 3/1992 | Leclef et al. |
| 5,118,528 A | 6/1992 | Fessi et al. |
| 5,145,684 A | 9/1992 | Liversidge et al. |
| 5,182,258 A | 1/1993 | Chiou |
| 5,188,837 A | 2/1993 | Domb |
| 5,192,528 A | 3/1993 | Radhakrishnan et al. |
| 5,236,707 A | 8/1993 | Stewart |
| 5,268,461 A | 12/1993 | Shoji et al. |
| 5,308,531 A | 5/1994 | Urfer et al. |
| 5,317,010 A | 5/1994 | Pang et al. |
| 5,369,095 A | 11/1994 | Kee et al. |
| 5,457,100 A | 10/1995 | Daniel |
| 5,550,220 A | 8/1996 | Meyer et al. |
| 5,560,932 A | 10/1996 | Bagchi et al. |
| 5,639,733 A | 6/1997 | Koike et al. |
| 5,661,130 A | 8/1997 | Meezan et al. |
| 5,662,883 A | 9/1997 | Bagchi et al. |
| 5,665,331 A | 9/1997 | Bagchi et al. |
| 5,716,642 A | 2/1998 | Bagchi et al. |
| 5,738,845 A | 4/1998 | Imakawa |
| 5,780,062 A | 7/1998 | Frank et al. |
| 5,789,375 A | 8/1998 | Mukae et al. |

(Continued)

FOREIGN PATENT DOCUMENTS

EP 0396777 A1 11/1990
EP 606046 7/1994

(Continued)

OTHER PUBLICATIONS

U.S. Appl. No. 60/148,464, filed Aug. 12, 1999, Noe.
Wermeling et al., "Pharmacokinetics and pharmacodynamics of a new intranasal midazolam formulation in healthy volunteers," Anesthesia & Analgesia 103 (2):344-349 (2006).
EP08747813 Supplementary Search Report dated Jun. 2, 2010.
PCT/US09/38696 Search Report dated Sep. 28, 2009.
PCT/US08/62961 Search Report dated Jul. 25, 2008.
PCT/US2012/042311 Search Report dated Aug. 31, 2012.
AU application 2009228093 First exam report dated Jul. 19, 2013.

(Continued)

*Primary Examiner* — Adam C Milligan
(74) *Attorney, Agent, or Firm* — Wilson Sonsini Goodrich & Rosati

(57) ABSTRACT

The invention relates to pharmaceutical compositions comprising one or more benzodiazepine drugs for nasal administration, methods for producing and for using such compositions.

22 Claims, 5 Drawing Sheets

(56) References Cited

U.S. PATENT DOCUMENTS

| | | |
|---|---|---|
| 5,795,896 A | 8/1998 | Löfroth et al. |
| 5,814,607 A | 9/1998 | Patton |
| 5,817,634 A | 10/1998 | Meezan et al. |
| 5,831,089 A | 11/1998 | Huber |
| 5,861,510 A | 1/1999 | Piscipio et al. |
| 5,863,949 A | 1/1999 | Robinson et al. |
| 5,955,425 A | 9/1999 | Morley et al. |
| 5,981,719 A | 11/1999 | Woiszwillo et al. |
| 6,004,574 A | 12/1999 | Backstrom et al. |
| 6,090,925 A | 7/2000 | Woiszwillo et al. |
| 6,143,211 A | 11/2000 | Mathiowitz et al. |
| 6,165,484 A | 12/2000 | Raad et al. |
| 6,193,985 B1 | 2/2001 | Sonne |
| 6,235,224 B1 | 5/2001 | Mathiowitz et al. |
| 6,254,854 B1 | 7/2001 | Edwards et al. |
| 6,268,053 B1 | 7/2001 | Woiszwillo et al. |
| 6,316,029 B1 | 11/2001 | Jain et al. |
| 6,316,410 B1 | 11/2001 | Barbier et al. |
| 6,375,986 B1 | 4/2002 | Ryde et al. |
| 6,395,300 B1 | 5/2002 | Straub et al. |
| 6,428,814 B1 | 8/2002 | Bosch et al. |
| 6,458,387 B1 | 10/2002 | Scott et al. |
| 6,461,591 B1 | 10/2002 | Keller et al. |
| 6,482,834 B2 | 11/2002 | Spada et al. |
| 6,495,498 B2 | 12/2002 | Niemiec et al. |
| 6,524,557 B1 | 2/2003 | Backstrom et al. |
| 6,607,784 B2 | 8/2003 | Kipp et al. |
| 6,610,271 B2 | 8/2003 | Wermeling |
| 6,616,914 B2 | 9/2003 | Ward et al. |
| 6,627,211 B1 | 9/2003 | Choi et al. |
| 6,794,357 B1 | 9/2004 | Backstrom et al. |
| 6,869,617 B2 | 3/2005 | Kipp |
| 6,884,436 B2 | 4/2005 | Kipp |
| 6,908,626 B2 | 6/2005 | Cooper et al. |
| 6,932,962 B1 | 8/2005 | Backstrom et al. |
| 6,991,785 B2 | 1/2006 | Frey |
| 7,008,920 B2 | 3/2006 | Kimura et al. |
| 7,037,528 B2 | 5/2006 | Kipp |
| 7,132,112 B2 | 11/2006 | Choi et al. |
| 7,434,579 B2 | 10/2008 | Young et al. |
| 8,530,463 B2 | 9/2013 | Cartt |
| 2001/0042932 A1 | 11/2001 | Mathiowitz et al. |
| 2002/0110524 A1 | 8/2002 | Cowan et al. |
| 2002/0127278 A1 | 9/2002 | Kipp |
| 2002/0141971 A1 | 10/2002 | Frey |
| 2002/0168402 A1 | 11/2002 | Kipp |
| 2003/0017203 A1 | 1/2003 | Crotts et al. |
| 2003/0031719 A1 | 2/2003 | Kipp |
| 2003/0040497 A1 | 2/2003 | Teng et al. |
| 2003/0087820 A1 | 5/2003 | Young et al. |
| 2003/0100755 A1 | 5/2003 | Sham et al. |
| 2003/0118547 A1 | 6/2003 | Vandenberg |
| 2003/0118594 A1 | 6/2003 | Nag et al. |
| 2003/0158206 A1 | 8/2003 | Billotte et al. |
| 2003/0170206 A1 | 9/2003 | Rasmussen et al. |
| 2003/0181411 A1 | 9/2003 | Bosch et al. |
| 2004/0115135 A1 | 6/2004 | Quay |
| 2004/0126358 A1 | 7/2004 | Warne et al. |
| 2004/0141923 A1 | 7/2004 | Dugger et al. |
| 2004/0147473 A1 | 7/2004 | Warriell, Jr. |
| 2004/0258663 A1 | 12/2004 | Quay et al. |
| 2005/0130260 A1 | 6/2005 | Linden et al. |
| 2005/0234101 A1 | 10/2005 | Stenkamp et al. |
| 2006/0045869 A1 | 3/2006 | Meezan et al. |
| 2006/0046962 A1 | 3/2006 | Meezan et al. |
| 2006/0046969 A1 | 3/2006 | Maggio |
| 2006/0106227 A1 | 5/2006 | Reddy et al. |
| 2006/0147386 A1 | 7/2006 | Wermeling |
| 2006/0198896 A1 | 9/2006 | Liversidge et al. |
| 2007/0059254 A1 | 3/2007 | Singh |
| 2007/0098805 A1 | 5/2007 | Liversidge |
| 2007/0298010 A1 | 12/2007 | Maggio |
| 2008/0200418 A1 | 8/2008 | Maggio |
| 2008/0248123 A1 | 10/2008 | Swanson et al. |
| 2008/0268032 A1 | 10/2008 | Maggio |
| 2008/0279784 A1 | 11/2008 | Cartt |
| 2008/0299079 A1 | 12/2008 | Meezan et al. |
| 2009/0047347 A1 | 2/2009 | Maggio |
| 2009/0130216 A1 | 5/2009 | Cartt |
| 2009/0163447 A1 | 6/2009 | Maggio |
| 2009/0258865 A1 | 10/2009 | Cartt et al. |
| 2009/0297619 A1 | 12/2009 | Swanson et al. |
| 2009/0304801 A1 | 12/2009 | Liversidge et al. |
| 2010/0068209 A1 | 3/2010 | Maggio |
| 2010/0203119 A1 | 8/2010 | Leane et al. |
| 2010/0209485 A1 | 8/2010 | Maggio |
| 2011/0172211 A1 | 7/2011 | Back et al. |
| 2011/0257096 A1 | 10/2011 | Maggio |
| 2012/0196941 A1 | 8/2012 | Maggio |
| 2013/0065886 A1 | 3/2013 | Cartt |

FOREIGN PATENT DOCUMENTS

| | | |
|---|---|---|
| EP | 00780386 | 6/1997 |
| EP | 0818442 | 1/1998 |
| EP | 931 788 | 7/1999 |
| EP | 0945485 | 9/1999 |
| EP | 1004578 | 5/2000 |
| EP | 1417972 A1 | 5/2004 |
| JP | 1-151528 | 6/1989 |
| JP | 2003-505403 | 2/2003 |
| JP | 2005-508939 | 4/2005 |
| JP | 2007-510722 | 4/2007 |
| WO | WO-9005719 | 5/1990 |
| WO | WO-91-19481 | 12/1991 |
| WO | WO-94-05262 A1 | 3/1994 |
| WO | WO-95-00151 A1 | 1/1995 |
| WO | WO-95-31217 A1 | 11/1995 |
| WO | WO-9627583 | 9/1996 |
| WO | WO-9633172 | 10/1996 |
| WO | WO-97-14407 A1 | 4/1997 |
| WO | WO-9803516 | 1/1998 |
| WO | WO-9807697 | 2/1998 |
| WO | WO-9830566 | 7/1998 |
| WO | WO-9833768 | 8/1998 |
| WO | WO-9834915 | 8/1998 |
| WO | WO-9834918 | 8/1998 |
| WO | WO-9907675 | 2/1999 |
| WO | WO-9929667 | 6/1999 |
| WO | WO-9952889 | 10/1999 |
| WO | WO-9952910 | 10/1999 |
| WO | WO-00-01390 A1 | 1/2000 |
| WO | WO-0074681 | 12/2000 |
| WO | WO-03-055464 | 7/2003 |
| WO | WO-2005-018565 A2 | 3/2005 |
| WO | WO-2005-044234 A2 | 5/2005 |
| WO | WO-2005-089768 | 9/2005 |
| WO | WO-2005-117830 A1 | 12/2005 |
| WO | WO-2006-025882 A2 | 3/2006 |
| WO | WO-2006-055603 | 5/2006 |
| WO | WO-2006-075123 A1 | 7/2006 |
| WO | WO-2006-088894 | 8/2006 |
| WO | WO-2007-043057 A2 | 4/2007 |
| WO | WO-2007-144081 A1 | 12/2007 |
| WO | WO-2008-027395 A2 | 3/2008 |
| WO | WO-2009-120933 A2 | 10/2009 |

OTHER PUBLICATIONS

EP application 09723906.5 Extended European search report dated Jun. 3, 2013.

JP application 2010-507633 Decision of refusal dated Jul. 9, 2013.

Ahsan et al., "Effects of the permeability enhancers, tetradecylmaltoside and dimethyl-β-cyclodextrin, on insulin movement acress human bronchial epithelial cells", European Journal of Pharmaceutical. Sciences, 2003; 20: 27-34.

Ahsan et al., "Sucrose cocoate, a component of cosmetic preparations enhances nasal and ocular peptide absorption", Int J Pharm, 2003; 251: 195-203.

Albert et al., "Pharmacokinetics of diphenhydramine in man", J. Pharmacokinet, Biopharm., 3(3):159-170 (1975).

Arnold et al., "Correlation of tetradecylmaltoside induced increases in nasal peptide drug delivery with morphological changes in nasal eithelial cells", J. Pharm. Sci. 93(9):2205-2213 (2004).

(56) References Cited

OTHER PUBLICATIONS

Beam et al., "Blood, Brain, Cerebrospinal Fluid Concentrations of Several Antobiotics in Rabbits with Intact and Inflamed Meninges", Antimicrobal Agents and Chemotherapy, Dec. 1977, pp. 710-716.
Bhairi S.M., "A guide to the properties and uses of detergents in biological systems", *Calbiochem*, pp. 1-42 (2001).
Birkett et al., "Bioavailability and First Pass Clearance", Australian Prescriber, 1991, pp. 14-16, vol. 14.
Birkett et al., "How Drugs are Cleared by the Liver", Australian Prescriber, 1990, pp. 88-89, vol. 13, No. 4.
CA 2,723,470 Office action dated Jun. 7, 2012.
Castro et al., "Ecologically safe alkyl glucoside-based gemini surfactants", ARKIVOC, xii:253-267 (2005).
Chavanpatil and Vavia, "Nasal drug delivery of sumatriptan succinate", Pharmazie., May 2005:60(5):347-349.
Chen et al., "Peptide Drug Permeation Enhancement by Select Classes of Lipids", presented ath the 45th American Society of Cell Biology, S.F., CA, Dec. 10-14, 2005; 1 page total.
Chen-Quay et al., "Identification of tight junction modulating lipids", J. Pharm. Sci., 98(2):606-619 (2009).
Chiou et al., "Improvement of Systemic Absorption of Insulin Through Eyes with Absorption Enhancers", Journal of Pharmaceutical Sciences, Oct. 1989, pp. 815-818, vol. 78, No. 10.
Chiou et al., "Systemic Delivery of Insulin Through Eyes to Lower the Glucose Concentration", Journal of Ocular Pharmacology, 1989, pp. 81-91, vol. 5, No. 1.
Chinese Patent Office from Application No. CN200980157305.0 dated Jan. 28, 2013.
Davis and Illum, "Absorption enhancers for nasal drug delivery", Clin. Pharmacokine., 2003:42(13):107-28.
De Vry and Schreiber, "Effects of selected serotonin 5-HT(1) and 5-HT(2) receptor agonists on feeding behavior: possible mechanisms of action", Neurosci. Biobehav. Rev., 24(3):341-53 (2000).
Definition downloaded Sep. 13, 2012 at the medical-dictionary.thefreedictionary.com/p/encephalin.
Definition of pilus, Merriam-Webster Medical Dictionary, http://www.merriam-webster.com/medical/pilus, accessed online on May 28, 2013.
Definition of villus, Merriam-Webster Medical Dictionary, http://www.merriam-webster.com/medical/villus, accessed online on May 28, 2013.
Drewe et al., "Enteral absorption of octreotide: absorption enhancement by polyoxyethylene-24-cholesterol ether", Br. J. Pharmacol., 108(2):298-303 (1993).
Duquesnoy et al., "Comparative clinical pharmacokinetics of single doses of sumatriptan following subcutaneous, oral, rectal and intranasal administration", Eur. J. Pharm. Sci., 6(2):99-104 (1998).
Edwards CM., "GLP-1: target for a new class of antidiabetic agents?", J.R. Soc. Med., 97(6):270-274 (2004).
Eley and Triumalashetty, "In vitro assessment of alkylglycosides as permeability enhancers", AAPS PharmsciTech., 2(3): article 19, pp. 1-7 (2001).
European Search Report (ESR) from EP 09 83 5809 dated Nov. 13, 2012.
Fricker et al., "Permeation enhancement of octreotide by specific bile salts in rats and human subjects: in vitro, in vivo correlations", Br. J. Pharmacol., 117(1):217-23 (1996).
Gordon et al., "Nasal Absorption of Insulin: Enhancement by Hydrophobic Bile Salts", Proceedings of the National Academy of Sciences of the United States of America, Nov. 1985, pp. 7419-7423, vol. 82.
Hathcox and Beuchat, "Inhibitory effects of sucrose fatty acid esters, alone and in combination with ethylenediaminetetraacetic acid and other organic acids, on viability of *Escherichia coli* 0157:H7", Food Microbiology, vol. 13, Issue 3, 213-225 (1996).
Hovgaard et al., "Insulin Stabilization and GI Absorption", Journal of Controlled Release, Mar. 1992, pp. 99-108, vol. 19, Issue 1-3.
Hovgaard et al., "Stabilization of insulin by alkylmaltosides. A. Spectroscopic evaluation", International Journal of Pharmaceutics, 132(1-2):107-113 (1996).
Hovgaard et al., "Stabilization of Insulin by Alkylmaltosides. B. Oral Absorption in Vivo in Rats", International Journal of Pharmaceutics, 1996, pp. 115-121, vol. 132.
International Search Report (ISR) from PCT/US2011/056735 dated Jun. 22, 2012.
JP2010-507633 Office Action dated Oct. 23, 2012.
Katzung, B., "Basic and Clinical Pharmacology, 7th Edition", Appleton & Lange: Stamford, Connecticut, 1998, pp. 34-49.
Lacy, C, et al., "Drug Information Handbook, 7th Edition 1999-2000" Lexi-Comp, Inc., 1999, pp. 163-164.
Lahat et al., "Intranasal midazolam for childhood seizures", The Lancet, 1998; 352: 620.
Lehninger et al., "Principles of Biochemistry with an Extended Discussion of Oxygen-Binding Proteins", 1982, pp. 150-151, Worth Publishers, Inc.
Maa and Prestrelski, "Biopharmaceutical powders: particle formation and formulation considerations", Curr. Pharm. Biotechnol., 1(3):283-302 (2000).
Material Safety Data Sheet for Anatrace, Inc. product n-Dodecyl-β-d-Maltopyranoside, Anagrade, Dated: Jan. 25, 1994 and Revised: Jul. 15, 2004, hhtp://media.affymetrix.com/estore/browse/level_three)category_and_products.jsp?category=35843 &categoryldClicked=35843&expand=true&parent=35900, access online on Dec. 13, 2012.
Mathew N.T., "Serotonin 1D (5-HT1D) agonists and other agents in acute migraine", Neurol. Clin., 15(1):61-83 (1997).
Matsumura et al., "Surface activities, biodegrabalbility and antimicrobial properties of n-alkyl glucosides, mannosides and galactosides", Journal of the America Oil Chemists' Society, 67(12):996-1001 (1990).
Moses et al., "Insulin Administered Intranasally as an Insulin-Bite Salt Aerosol—Effectiveness and Reproducibility in Normal and Diabetic Subjects", Diabetes, Nov. 1983, pp. 1040-1047, vol. 32.
Murakami et al., "Assessment of Enhancing AbititY of Medium-Chain Alkyl Saccharides as New Absorption Enhancers in Rat Rectum", International Journal of Pharmaceutics, Feb. 1992, pp. 159-169, vol. 79, Issue 1-3].
Ogiso et al., "Percutaneous Absorption of Elcatonin Chemical and Hypocalcemic Effect in Rat", Chemical & Pharmaceutical Bulletin, Feb. 1991, pp. 449-453, vol. 39, Issue 2, The Pharmaceutical Society of Japan, Tokyo, Japan.
Olesen et al., "The Headaches", *Lippincott Williams & Wilkins*, p. 474 (2005).
Paulsson and Edsman, "Controlled drug release from Gels using surfactant aggregates. II Vesicles formed from mixtures of amphiphilic drugs and oppositely charged surfactants", Pharm, Res., 18(11):1586-1592 (2001).
PCT/US08/62961 International Preliminary Report on Patentability dated Nov. 10, 2009.
PCT/US09/38696 International Preliminary Report on Patentability dated Sep. 28, 2010.
Phillips, A., "The challenge of gene therapy and DNA delivery", J. Pharm Pharmacology 53: 1169-1174, 2001.
Pillion et al., "Synthetic long-chain alkyl maltosidee and alkyl sucrose esters as enhancers of nasal insulin absorption", J. Pharm. Sci., 91:1456-1462 (2002).
Pillion et al., "Systemic Absorption of Insulin Delivered Topically to the Rat Eye", Investigative Ophthalmology & Visual Science, Nov. 1991, pp. 3021-3027, vol. 32, Issue 12.
Pirollo et al., "Targeted Delivery of Small Interfering RNA: Approaching Effective Cancer Therapies", Cancer Res. 68(5): 1247-1250, 2008.
Richards R.M., "Inactivation of resistant *Pseudomonas aeruginosa* by antibacterial combinations", J. Pharm. Pharmacol., 23:136S-140S (1971).
Salzman et al., "Intranasal Aerosolized Insulin", The New England Journal of Medicine, Apr. 25, 1985, pp. 1078-1084, vol. 312, Issue 17.
Sanders et al., "Pharmacokinetics of ergotamine in healthy volunteers following oral and rectal dosing", Eur. J. Clin. Pharmacol., 30(3):331-334 (1986).

(56) References Cited

OTHER PUBLICATIONS

Shim and Kim, "Administration Route Dependent Bioavailability of Interferon-α and Effect of Bile Salts on the Nasal Absorption", Drug Development and Industrial Pharmacy, 19(10):1183-1199 (1993).
Stevens and Guillet, "Use of Glucagon to Treat Neonatal Low-Output Congestive Heart Failure after Maternal Labetalol Therapy", The Journal of Pediatrics, Jul. 1995, pp. 151-153, vol. 127, Issue 1.
Swarbrick et al., Encyclopedia of Pharmaceutical Technology, Informa Health Care, 2nd edition, vol. 1, p. 918 (2002).
Tsuchido et al,, "Lysis of *Bacillus subtilis* Cells by Glycerol and Sucrose Esters of Fatty Acids", Applied and Environmental Microbiology. vol. 53, No. 3, 505-508, 1987.
Türker et al., "Nasal route and drug delivery systems", Pharm. World Sci., 26(3):137-42 (2004).
Turton et al., "A role for glucagon-like peptide-1 in the central regulation of feeding", Nature, 1996; 379:69-72.
U.S. Appl. No. 12/116,842 Office action mailed May 25, 2011.
U.S. Appl. No. 12/116,842 Office action mailed Apr. 2, 2013.
U.S. Appl. No. 12/116,842 Office action mailed Nov. 15, 2011.
U.S. Appl. No. 12/116,842 Office action mailed Dec. 17, 2013.
U.S. Appl. No. 12/266,529 Office action mailed Jul. 10, 2012.
U.S. Appl. No. 12/266,529 Office action mailed Nov. 16, 2011.
U.S. Appl. No. 12/413,439 Office action mailed Mar. 18, 2011.
U.S. Appl. No. 12/413,439 Office action mailed Nov. 21, 2011.
Vidal et al., "Making sense of antisense", European Journal of Cancer, 41:2812-2818, 2005.
Watanabe et al., "Antibacterial Carbohydrate Monoesters Suppressing Cell Growth of Streptoccus mutans in the Presence of Sucrose", Current Microbiology, Sep. 2000, pp. 210-213, vol. 41, No. 3.
Weber and Benning, "Metabolism of orally administered alkyl beta-glycosides in the mouse", J. Nutr., 114:247-254 (1984).
Webpage for Anatrace products of Affymetrix, http://www.affymetrix.com/estore/browse/level_three_category_and_products.jsp?category=35843&categoryldClicked=35843&expand=true&parent=35900, accessed online on Dec. 13, 2012.
Yamamoto et al., "The Ocular Route for Systemic Insulin Delivery in the Albino Rabbit", The Journal of Pharmacology and Experimental Therapeutics, Apr. 1989, pp. 249-255, vol. 249; No. 1.
Yu Xinrui et al., "Triptan Medicament and Migraine", World Pharmacy (Synthetic Drug and Biochemical Drug Formulation Fascicule), 22(2):91-92 (2001).
Fix, "Oral controlled release technology for peptides: status and future prospects", Pharmaceutical Research Dec. 1996;13(12):1760-1764.
Hussain et al, "Absorption enhancers in pulmonary protein delivery." J Control Release. Jan. 8, 2004;94(1):15-24.
Kissel et al., "Tolerability and absorption enhancement of intranasally administered octreotide by sodium taurodihydrofusidate in healthy subjects." Pharm Res. Jan. 1992;9(1):52-57.
Kite et al., "Use of in vivo-generated biofilms from hemodialysis catheters to test the efficacy of a novel antimicrobial catheter lock for biofilm eradication in vitro." J Clin Microbiol. Jul. 2004;42(7):3073-3076.
Liu et al., "Interaction between chitosan and alkyl P-D-glucopyranoside and its effect on their antimicrobial activity", Carbohydrate Polymers. 2004; 56: 243-250.
U.S. Appl. No. 12/413,439 Office action mailed Jun. 19, 2014.

Figure 4: Flow Diagram for the Manufacture of Diazepam Solution
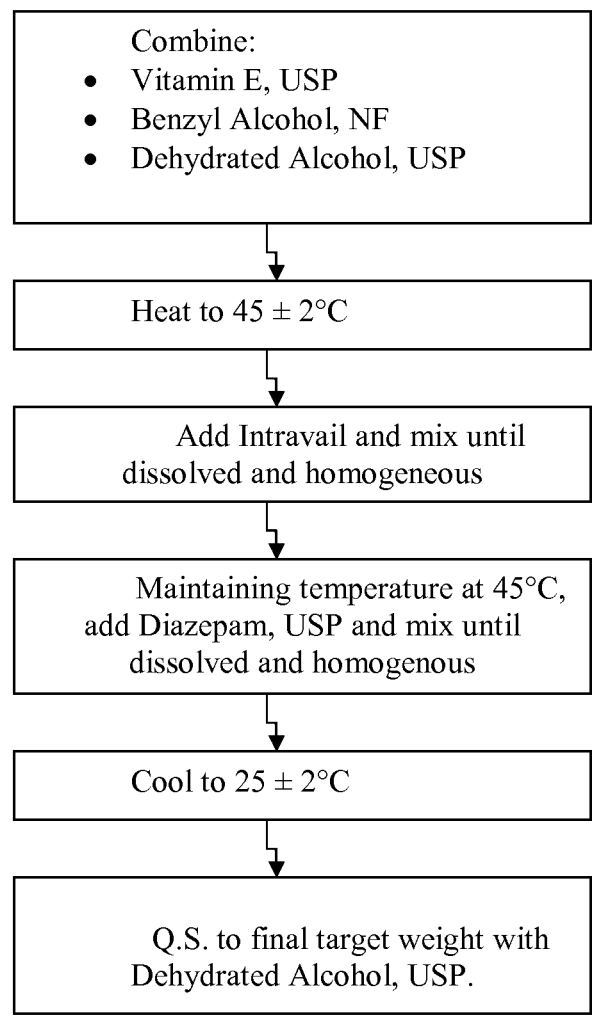

Figure 5: Flow Diagram for Preparation of Diazepam Suspension
Flow Diagram for the Manufacture of NRL-1A
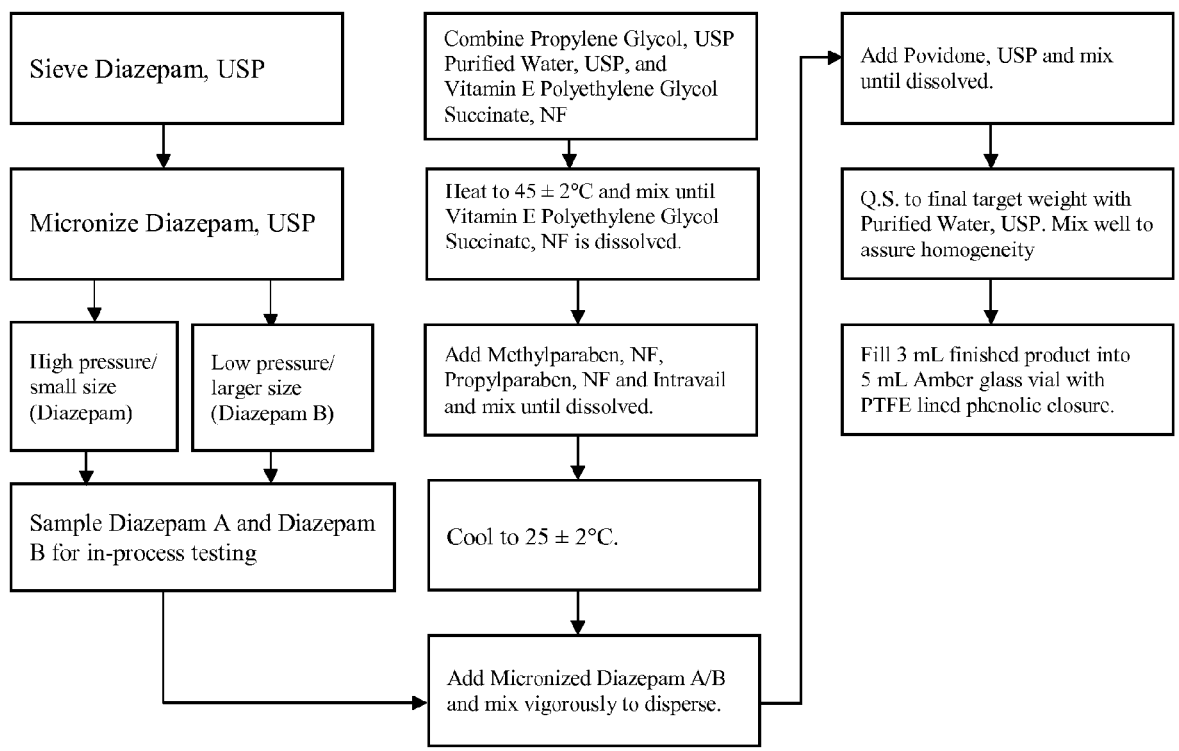

ADMINISTRATION OF BENZODIAZEPINE COMPOSITIONS

CROSS-REFERENCE TO RELATED APPLICATIONS

This application is a Continuation-in-Part of U.S. patent application Ser. No. 12/413,439, filed Mar. 27, 2009, published as US 2009/0258865 on Oct. 15, 2009, which is incorporated herein by reference in its entirety; this application also claims priority to U.S. provisional application 61/040,558, filed Mar. 28, 2008, U.S. provisional application 61/497,017, filed Jun. 14, 2011 and U.S. provisional application 61/570,110, filed Dec. 13, 2011, each of which is incorporated herein by reference in its entirety.

FIELD OF THE INVENTION

This application relates to the nasal administration of benzodiazepine drugs and combinations thereof.

BACKGROUND OF THE INVENTION

By way of non-limiting example, the benzodiazepine family consists of drugs such as diazepam, lorazepam, and midazolam. The drugs in this family have been observed as possessing sedative, tranquilizing and muscle relaxing properties. They are frequently classified as anxiolytic and skeletal muscle relaxants. They are thought to be useful in preventing, treating, or ameliorating the symptoms of anxiety, insomnia, agitation, seizures (such as those caused by epilepsy), muscle spasms and rigidity, the symptoms of drug withdrawal associated with the continuous abuse of central nervous system depressants, and exposure to nerve agents.

Benzodiazepines are thought to act by binding to the $GABA_A$ receptor of a neuron, possibly causing the receptor to change shape and making it more accessible to gamma-aminobutyric acid (GABA).

GABA is an inhibitory neurotransmitter that, when bound to the $GABA_A$ receptor, facilitates $Cl^-$ ions flooding into the neuron to which the receptor is bound. The increase in $Cl^-$ ions hyperpolarizes the membrane of the neuron. This completely or substantially reduces the ability of the neuron to carry an action potential. Targeting this receptor is particularly useful in treating many disorders, such as tetanus and epilepsy, which may result from too many action potentials proceeding through the nervous system.

Current formulations of benzodiazepine drugs can be administered orally, rectally, or parenterally. The ability to utilize these and other types of formulations has been significantly limited due, in many cases, to solubility challenges.

The oral route of administration may be considered suboptimal due to several disadvantages. For example, the amount of time required for an orally administered benzodiazepine drug to reach therapeutically relevant concentrations in blood plasma may be rather long, such as an hour or more. Moreover, as benzodiazepine drugs pass through the liver a significant amount of the drug may be metabolized. Thus, large doses may be required to achieve therapeutic plasma levels. Furthermore, due to the nature of seizures and muscle spasms, it can be extremely difficult for either a patient or a care-giver to administer the benzodiazepine drug orally and care-givers may be reluctant to place their hands in patients' mouths.

Intravenous administration perhaps provides a faster route of administration. However intravenous administration is generally limited to trained health care professionals in tightly controlled clinical settings. Additionally, sterility must be maintained. Furthermore, administering any drug intravenously can be painful and is likely impractical for patients suffering from a phobia of needles. In addition, intravenous administration of benzodiazepines is associated with respiratory depression. Thus, use of intravenous benzodiazepines is limited to professional health care environments.

Rectal suppository compositions of benzodiazepine drugs can have a rapid onset of action. However, the inconvenience of rectally administered drug is an obvious impediment to their being administered by anyone outside a very small group of the patient's intimate acquaintances and the patient's professional medical care-givers.

SUMMARY OF THE INVENTION

In some embodiments, there are provided (non-aqueous) pharmaceutical solutions for nasal administration consisting of: (a) a benzodiazepine drug; (b) one or more natural or synthetic tocopherols or tocotrienols, or any combinations thereof, in an amount from about 30% to about 95% (w/w); (c) one or more alcohols or glycols, or any combinations thereof, in an amount from about 10% to about 70% (w/w); and (d) an alkyl glycoside, in a pharmaceutically-acceptable solution for administration to one or more nasal mucosal membranes of a patient. In some embodiments, the benzodiazepine drug is dissolved in the one or more natural or synthetic tocopherols or tocotrienols, or any combinations thereof, in an amount from about 30% to about 95% (w/w); and the one or more alcohols or glycols, or any combinations thereof, in an amount from about 10% to about 70% (w/w). In some embodiments, the benzodiazepine drug is selected from the group consisting of: alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, any pharmaceutically-acceptable salts thereof, and any combinations thereof. In some embodiments, the benzodiazepine drug is diazepam, or a pharmaceutically-acceptable salt thereof. In some embodiments, the solution contains about 1 to about 20% (w/v) of benzodiazepine, e.g. about 1 to about 20% (w/v) of diazepam. In some embodiments, the one or more natural or synthetic tocopherols or tocotrienols are selected from the group consisting of α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof. In some embodiments, the one or more alcohols are selected from the group consisting of ethanol, propyl alcohol, butyl alcohol, pentanol, benzyl alcohol, any isomers thereof, or any combinations thereof. In some embodiments, the solution contains two or more alcohols, such as ethanol (1-25% (w/v)) and benzyl alcohol (1-25% (w/v)), or ethanol (10-22.5% (w/v)) and benzyl alcohol (7.5-12.5% (w/v)). In some embodiments, the benzodiazepine is present in the pharmaceutical composition in a concentration from about 20 mg/mL to about 200 mg/mL. In some embodiments, the one or more natural or synthetic tocopherols or tocotrienols, or any combinations thereof, is in an amount from about 45% to about 85% (w/w). In some embodiments, the one or more natural or synthetic tocopherols or tocotrienols, or any combinations thereof, is in an amount from about 50% to about 75% (w/w). In some embodiments, the one or more alcohols or glycols, or any combinations thereof, is in an amount from about 15% to about 55% (w/w), e.g. about 25% to about 40%

(w/w). In some embodiments, the solution consists of diazepam (5-15% (w/v)), alkyl glycoside (0.01-1% (w/v)), vitamin E (45-65% (w/v)), ethanol (10-25% (w/v)) and benzyl alcohol (5-15% (w/v)). In some embodiments, the solution comprises at least about 0.01% (w/w) of an alkyl glycoside, e.g. about 0.01% to 1% (w/w) of an alkyl glycoside, such as dodecyl maltoside. In some embodiments, the solution consists of diazepam (5-15% (w/v)), dodecyl maltoside (0.01-1% (w/v)), vitamin E (45-65% (w/v)), ethanol (10-25% (w/v)) and benzyl alcohol (5-15% (w/v)); more particularly the solution may consist of diazepam (9-11% (w/v)), dodecyl maltoside (0.1-0.5% (w/v)), vitamin E (50-60% (w/v)), ethanol (15-22.5% (w/v)) and benzyl alcohol (7.5-12.5% (w/v)); and even more particularly, the solution may consist of diazepam (10% (w/v)), dodecyl maltoside (0.15-0.3% (w/v)), vitamin E (50-60% (w/v)), ethanol (17-20% (w/v)) and benzyl alcohol (10-12% (w/w)).

Some embodiments described herein provide a method of treating a patient with a disorder which may be treatable with a benzodiazepine drug, comprising: administering to one or more nasal mucosal membranes of a patient a pharmaceutical solution for nasal administration consisting of a benzodiazepine drug, one or more natural or synthetic tocopherols or tocotrienols, or any combinations thereof, in an amount from about 30% to about 95% (w/w); one or more alcohols or glycols, or any combinations thereof, in an amount from about 10% to about 70% (w/w); and an alkyl glycoside. In some embodiments, the benzodiazepine drug is dissolved in the one or more natural or synthetic tocopherols or tocotrienols, or any combinations thereof, in an amount from about 30% to about 95% (w/w); and the one or more alcohols or glycols, or any combinations thereof, in an amount from about 10% to about 70% (w/w). In some embodiments, the benzodiazepine drug is selected from the group consisting of: alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, any pharmaceutically-acceptable salts thereof, and any combinations thereof. In some embodiments, the benzodiazepine drug is diazepam, or a pharmaceutically-acceptable salt thereof. In some embodiments, the solution contains about 1 to about 20% (w/v) of benzodiazepine, e.g. about 1 to about 20% (w/v) of diazepam. In some embodiments, the one or more natural or synthetic tocopherols or tocotrienols are selected from the group consisting of α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof. In some embodiments, the one or more alcohols are selected from the group consisting of ethanol, propyl alcohol, butyl alcohol, pentanol, benzyl alcohol, any isomers thereof, or any combinations thereof. In some embodiments, the solution contains two or more alcohols, such as ethanol (1-25% (w/v)) and benzyl alcohol (1-25% (w/v)), or ethanol (10-22.5% (w/v)) and benzyl alcohol (7.5-12.5% (w/v)). In some embodiments, the benzodiazepine is present in the pharmaceutical composition in a concentration from about 20 mg/mL to about 200 mg/mL. In some embodiments, the one or more natural or synthetic tocopherols or tocotrienols, or any combinations thereof, is in an amount from about 45% to about 85% (w/w). In some embodiments, the one or more natural or synthetic tocopherols or tocotrienols, or any combinations thereof, is in an amount from about 50% to about 75% (w/w). In some embodiments, the one or more alcohols or glycols, or any combinations thereof, is in an amount from about 15% to about 55% (w/w), e.g. about 25% to about 40% (w/w). In some embodiments, the solution consists of diazepam (5-15% (w/v)), alkyl glycoside (0.01-1% (w/v)), vitamin E (45-65% (w/v)), ethanol (10-25% (w/v)) and benzyl alcohol (5-15% (w/v)). In some embodiments, the solution comprises at least about 0.01% (w/w) of an alkyl glycoside, e.g. about 0.01% to 1% (w/w) of an alkyl glycoside, such as dodecyl maltoside. In some embodiments, the solution consists of diazepam (5-15% (w/v)), dodecyl maltoside (0.01-1% (w/v)), vitamin E (45-65% (w/v)), ethanol (10-25% (w/v)) and benzyl alcohol (5-15% (w/v)); more particularly the solution may consist of diazepam (9-11% (w/v)), dodecyl maltoside (0.1-0.5% (w/v)), vitamin E (50-60% (w/v)), ethanol (15-22.5% (w/v)) and benzyl alcohol (7.5-12.5% (w/v)); and even more particularly, the solution may consist of diazepam (10% (w/v)), dodecyl maltoside (0.15-0.3% (w/v)), vitamin E (50-60% (w/v)), ethanol (17-20% (w/v)) and benzyl alcohol (10-12% (w/v)). In some embodiments, the patient is human. In some embodiments, the benzodiazepine is administered in a therapeutically effective amount from about 1 mg to about 20 mg. In some embodiments, the benzodiazepine is administered as in a dosage volume from about 10 μL to about 200 μL. In some embodiments, the administration of the pharmaceutical composition comprises spraying at least a portion of the therapeutically effective amount of the benzodiazepine into at least one nostril. In some embodiments, the administration of the pharmaceutical composition comprises spraying at least a portion of the therapeutically effective amount of the benzodiazepine into each nostril. In some embodiments, administration of the pharmaceutical composition comprises spraying a first quantity of the pharmaceutical composition into the first nostril, spraying a second quantity of the pharmaceutical composition into a second nostril, and optionally after a preselected time delay, spraying a third quantity of the pharmaceutical composition into the first nostril. In some embodiments, the method further comprises, optionally after a preselected time delay, administering at least a fourth quantity of the pharmaceutical composition to the second nostril. In some embodiments, nasal administration of the pharmaceutical composition begins at any time before or after onset of symptoms of a disorder which may be treatable with the pharmaceutical composition. In some embodiments, the treatment achieves bioavailability that is from about 80-125% (e.g. about 90-110%, or more particularly about 92.5-107.5%) of that achieved with the same benzodiazepine administered intravenously, e.g. In this context, it is intended that bioavailability be determined by a suitable pharmacodynamic method, such as comparison of area under the blood plasma concentration curve (AUC) for the nasally and intravenously administered drug. It is further understood that the percent bioavailability of the nasally administered benzodiazepine may be determined by comparing the area under the blood plasma concentration curve obtained with one dose of the benzodiazepine (e.g. 10 mg of nasal diazepam) with another dose of the same benzodiazepine administered intravenously (e.g. 5 mg of i.v. diazepam), taking into consideration the difference in dose. Thus, for the sake of illustration, a 10 mg nasal diazepam dose that achieves an AUC that is precisely half of the AUC obtained with 5 mg of i.v. diazepam would have a bioavailability of 100%. In some embodiments, the disorder to be treated is a seizure, such as an epileptic seizure, a breakthrough seizure, or other seizure. In some embodiments, the solution and treatment with the solution are substantially non-irritating and well-tolerated.

In some embodiments, the pharmaceutical composition for nasal administration comprises: a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 5% to about 70% (w/w), preferably about 10% to about 70% (w/w) in a pharmaceutically-acceptable formulation for administration to one or more nasal mucosal membranes of the patient. In some embodiments the benzodiazepine drug is dissolved in the one or more natural or synthetic tocopherols or tocotrienols, or any combinations thereof, in an amount from about 30% to about 95% (w/w); and the one or more alcohols or glycols, or any combinations thereof, in an amount from about 5% to about 70% (w/w), preferably about 10% to about 70% (w/w). In some embodiments, the benzodiazepine drug is dissolved in a carrier system. In some embodiments, at least part of the benzodiazepine drug is in a form comprising benzodiazepine microparticles, nanoparticles or combinations thereof. In some embodiments, the composition is substantially free of benzodiazepine microparticles, nanoparticles or combinations thereof.

In some embodiments, the benzodiazepine drug is selected from the group consisting of alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, any pharmaceutically-acceptable salts thereof, and any combinations thereof. In some embodiments, the benzodiazepine drug is diazepam, or a pharmaceutically-acceptable salt thereof. In some embodiments, the benzodiazepine drug comprises benzodiazepine microparticles, nanoparticles, or combinations thereof. In some embodiments, the benzodiazepine nanoparticles have an effective average particle size of less than about 5000 nm. In some embodiments, the benzodiazepine drug is substantially free of benzodiazepine microparticles, nanoparticles or combinations thereof.

In some embodiments, the one or more natural or synthetic tocopherols or tocotrienols are selected from the group consisting of α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof. In some embodiments, a synthetic tocopherol can include Vitamin E TPGS (Vitamin E polyethylene glycol succinate). In some embodiments, on the other hand, synthetic tocopherols exclude tocopherols covalently bonded or linked (e.g. through a diacid linking group) to a glycol polymer, such as polyethylene glycol). Thus, in some embodiments, the compositions described herein exclude Vitamin E TPGS.

In some embodiments, one or more alcohols are selected from the group consisting of: ethanol, propyl alcohol, butyl alcohol, pentanol, benzyl alcohol, any isomers thereof, or any combinations thereof. In some embodiments, the one or more glycols are selected from the group consisting of: ethylene glycol, propylene glycol, butylene glycol, pentylene glycol, any isomers thereof, and any combinations thereof. In some preferred embodiments, the glycols exclude glycol polymers. In some preferred embodiments, the glycols exclude glycol polymers having an average molecular weight of greater than 200. In some embodiments, the glycols exclude polyethylene glycol having an average molecular weight of greater than about 200.

In some embodiments, the benzodiazepine drug is present in the carrier system in a concentration from about 1 mg/mL to about 600 mg/mL. In some embodiments, the benzodiazepine drug is present in a carrier system in a concentration from about 10 mg/mL to about 250 mg/mL. In some embodiments, the benzodiazepine is present in a carrier system in a concentration from about 20 mg/mL to about 50 mg/mL.

In some embodiments, the carrier system comprises one or more natural or synthetic tocopherols or tocotrienols, or any combinations thereof, in an amount from about 45% to about 85% (w/w). In some embodiments, the carrier system comprises one or more natural or synthetic tocopherols or tocotrienols, or any combinations thereof, in an amount from about 60% to about 75% (w/w). In some embodiments, the carrier system comprises one or more natural or synthetic tocopherols or tocotrienols, or any combinations thereof, in an amount of about 70% (w/w).

In some embodiments, the carrier system comprises one or more alcohols or glycols, or any combinations thereof, in an amount from about 10% to about 70% (w/w). In some embodiments, the carrier system comprises one or more alcohols or glycols, or any combinations thereof, in an amount from about 15% to about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount of about 30% (w/w).

In some embodiments, the composition comprises at least one additional ingredient selected from the group consisting of active pharmaceutical ingredients; enhancers; excipients; and agents used to adjust the pH, buffer the composition, prevent degradation, and improve appearance, odor, or taste.

In some embodiments, the composition comprises one or more additional excipients, such as one or more parabens, one or more povidones, and/or one or more alkyl glycosides.

The invention also discloses a method of treating a patient with a disorder that may be treatable with a benzodiazepine drug. In some embodiments, the patient is a human. In some embodiments, the method comprises: administering to one or more nasal mucosal membranes of a patient a pharmaceutical composition for nasal administration comprising a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 5% to about 70%, preferably about 10% to about 70% (w/w). In some embodiments, the benzodiazepine is dissolved in the one or more natural or synthetic tocopherols or tocotrienols, or any combinations thereof, in an amount from about 30% to about 95% (w/w); and the one or more alcohols or glycols, or any combinations thereof, in an amount from about 5% to about 70%, preferably about 10% to about 70% (w/w). In some embodiments, the benzodiazepine drug is dissolved in a carrier system. In some embodiments, the benzodiazepine drug includes benzodiazepine microparticles, nanoparticles, or combinations thereof. In some embodiments, the composition is substantially free of benzodiazepine microparticles, nanoparticles or combinations thereof.

In some embodiments, the benzodiazepine drug is selected from the group consisting of alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, or any pharmaceutically-acceptable salts thereof, and any combinations thereof. In some embodiments, the benzodiazepine drug is diazepam, or a pharmaceutically-acceptable salt thereof. In some embodiments, the benzodiazepine drug is fully dissolved in a single phase comprising one or more one or more natural or synthetic tocopherols or tocotrienols and one or more alcohols or glycols. In some embodiments, the benzodiazepine drug comprises benzodiazepine microparticles, nanoparticles, or combinations thereof. In some such embodiments, the composition further comprises water. In some embodiments, the benzodiazepine nanoparticles have an effective average particle size of less than about 5000 nm. In some embodiments, the composition is substantially free of benzodiazepine microparticles, nanoparticles or combinations thereof.

In some embodiments, the one or more natural or synthetic tocopherols or tocotrienols are selected from the group consisting of α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof.

In some embodiments, the one or more alcohols are selected from the group consisting of: ethanol, propyl alcohol, butyl alcohol, pentanol, benzyl alcohol, any isomers thereof, and any combinations thereof. In some embodiments, the one or more glycols are selected from the group consisting of ethylene glycol, propylene glycol, butylene glycol, pentylene glycol, any isomers thereof, and any combinations thereof. In some embodiments, the alcohol or glycol is free of water (dehydrated, USP). In some embodiments, the alcohol is ethanol (dehydrated, USP).

In some embodiments, the benzodiazepine drug is present in the carrier system in a concentration from about 1 mg/mL to about 600 mg/mL. In some embodiments, the benzodiazepine drug is present in the carrier system in a concentration of from about 10 mg/mL to about 250 mg/mL. In some embodiments, the benzodiazepine drug is present in the carrier system in a concentration of from about 20 mg/mL to about 50 mg/mL.

In some embodiments, the carrier system comprises one or more natural or synthetic tocopherols or tocotrienols, or any combinations thereof, in an amount from about 45% to about 85% (w/w). In some embodiments, the carrier system comprises one or more natural or synthetic tocopherols or tocotrienols, or any combinations thereof, in an amount from about 60% to about 75% (w/w). In some embodiments, the carrier system comprises one or more natural or synthetic tocopherols or tocotrienols, or any combinations thereof, in an amount of about 70% (w/w).

In some embodiments, the carrier system comprises one or more alcohols or glycols, or any combinations thereof, in an amount from about 15% to about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount from about 30% (w/w).

In some embodiments, the composition comprises at least one additional ingredient selected from the group consisting of active pharmaceutical ingredients; enhancers; excipients; and agents used to adjust the pH, buffer the composition, prevent degradation, and improve appearance, odor, or taste.

In some embodiments, the composition is in a pharmaceutically-acceptable spray formulation, and further comprising administering the composition to one or more nasal mucosal membranes of the patient. In some embodiments, the therapeutically effective amount is from about 1 mg to about 20 mg of the benzodiazepine. In some embodiments, the pharmaceutical composition is in a pharmaceutically-acceptable spray formulation having volume from about 10 μL to 200 μL.

In some embodiments, the administration of the composition comprises spraying at least a portion of the therapeutically effective amount of the composition into at least one nostril. In some embodiments, the administration of the composition comprises spraying at least a portion of the therapeutically effective amount of the composition into each nostril. In some embodiments, the administration of the composition comprises spraying a first quantity of the composition into the first nostril, spraying a second quantity of the composition into a second nostril, and optionally after a pre-selected time delay, spraying a third quantity of the composition into the first nostril. Some embodiments further comprise, optionally after a pre-selected time delay, administering at least a fourth quantity of the composition to the second nostril.

In some embodiments, the administration of the composition begins at any time before or after onset of symptoms of a disorder which may be treatable with the composition.

Additional embodiments, uses, and advantages of the invention will become apparent to the person skilled in the art upon consideration of the disclosure set forth herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Some embodiments of the invention may be further appreciated upon consideration of the appended drawings, of which:

FIG. 4 is a Flow Diagram for one embodiment of a process for the manufacture of a diazepam solution according to the instant invention.

FIG. 5 is a Flow Diagram for one embodiment of a process for the manufacture of a diazepam suspension according to the instant invention.

DETAILED DESCRIPTION OF THE INVENTION

Figure 1:
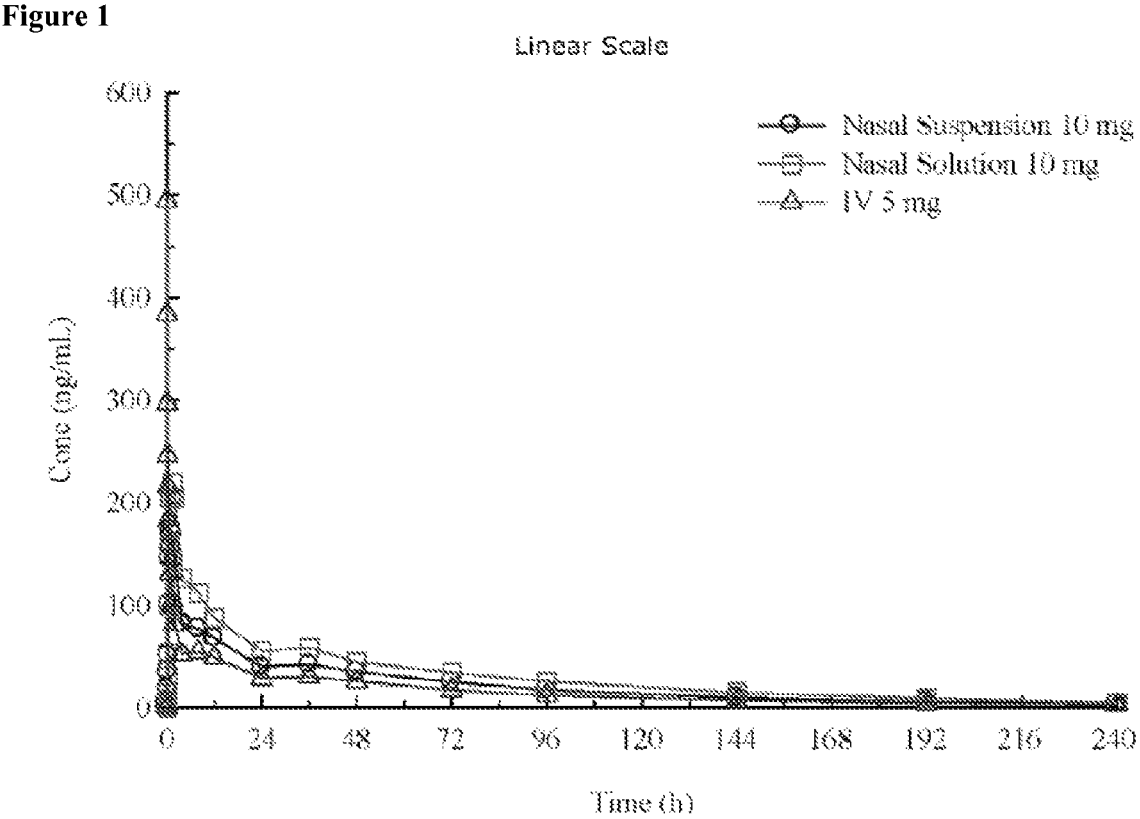
FIG. 1 depicts a 240 hour linear plot of the arithmetic mean plasma concentration of diazepam after intranasal administration of 10 mg of diazepam as a suspension of Table 11-2, intranasal administration 10 mg of diazepam as a solution of Table 11-1, and 5 mg of diazepam as an intravenous injection.

Provided herein are pharmaceutical compositions of one or more benzodiazepine drugs and methods of using such pharmaceutical compositions. Such pharmaceutical compositions are administered nasally.

In some embodiments, the pharmaceutical composition for nasal administration comprises: a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 10% to about 70% (w/w) in a pharmaceutically-acceptable formulation for administration to one or more nasal mucosal membranes of the patient. In some embodiments the benzodiazepine drug is dissolved in the one or more natural or synthetic tocopherols or tocotrienols, or any combinations thereof, in an amount from about 30% to about 95% (w/w); and the one or more alcohols or glycols, or any combinations thereof, in an amount from about 10% to about 70% (w/w). In some embodiments, the benzodiazepine drug is dissolved in a carrier system. In some embodiments, at least part of the benzodiazepine drug is in a form of microparticles, nanoparticles, or combinations thereof. In some embodiments, the composition is substantially free of benzodiazepine microparticles, nanoparticles or combinations thereof.

In some embodiments, the pharmaceutical composition for nasal administration comprises: a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 5% to about 70% (w/w) in a pharmaceutically-acceptable formulation for administration to one or more nasal mucosal membranes of the patient. In some embodiments the benzodiazepine drug is dissolved in the one or more natural or synthetic tocopherols or tocotrienols, or any combinations thereof, in an amount from about 30% to about 95% (w/w); and the one or more alcohols or glycols, or any combinations thereof, in an amount from about 5% to about 70% (w/w). In some embodiments, the benzodiazepine drug is dissolved in a carrier system. In some embodiments, at least part of the benzodiazepine drug is in a form of microparticles, nanoparticles, or combinations thereof. In some embodiments, the composition is substantially free of benzodiazepine microparticles, nanoparticles or combinations thereof.

In some embodiments, the benzodiazepine drug is selected from the group consisting of alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, any pharmaceutically-acceptable salts thereof, and any combinations thereof. In some embodiments, the benzodiazepine drug is diazepam, or a pharmaceutically-acceptable salt thereof. In some embodiments, the benzodiazepine drug comprises benzodiazepine microparticles, nanoparticles, or combinations thereof. In some embodiments, the benzodiazepine nanoparticles have an effective average particle size of less than about 5000 nm. In some embodiments, the composition is substantially free of benzodiazepine microparticles, nanoparticles or combinations thereof.

In some embodiments, the one or more natural or synthetic tocopherols or tocotrienols are selected from the group consisting of α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof. The carrier system includes one or more synthetic tocopherols having a polymer glycol covalently bonded or linked to a tocopherol core, such as Vitamin E TPGS, which is described in U.S. Pat. No. 6,193,985, which is incorporated herein by reference in its entirety. In particular, it has been found that in some particulate suspensions of benzodiazepines, wherein the benzodiazepine is not dissolved in a tocopherol phase, Vitamin E TPGS can be a desirable excipient for stabilizing the particulate (microparticle, nanoparticle or combination) suspension. In some embodiments, on the other hand, the carrier system specifically excludes synthetic tocopherols having a polymer glycol covalently bonded or linked to a tocopherol core, such as Vitamin E TPGS, which is described in U.S. Pat. No. 6,193,985, which is incorporated herein by reference in its entirety.

In some embodiments, one or more alcohols are selected from the group consisting of ethanol, propyl alcohol, butyl alcohol, pentanol, benzyl alcohol, any isomers thereof, or any combinations thereof. In some embodiments, the alcohol is ethanol (dehydrated, USP). In some embodiments, the one or more glycols are selected from the group consisting of ethylene glycol, propylene glycol, butylene glycol, pentylene glycol, any isomers thereof, and any combinations thereof. In some embodiments, the glycol is propylene glycol USP. In some embodiments, a synthetic tocopherol can include Vitamin E TPGS (Vitamin E polyethylene glycol succinate). In some embodiments, on the other hand, synthetic tocopherols exclude tocopherols covalently bonded or linked (e.g. through a diacid linking group) to a glycol polymer, such as polyethylene glycol). Thus, in some embodiments, the compositions described herein exclude Vitamin E TPGS.

In some embodiments, the benzodiazepine drug is present in the carrier system in a concentration from about 1 mg/mL to about 600 mg/mL. In some embodiments, the benzodiazepine drug is present in a carrier system in a concentration from about 10 mg/mL to about 250 mg/mL. In some embodiments, the benzodiazepine is present in a carrier system in a concentration from about 20 mg/mL to about 50 mg/mL.

In some embodiments, the carrier system comprises one or more natural or synthetic tocopherols or tocotrienols, or any combinations thereof, in an amount from about 45% to about 85% (w/w). In some embodiments, the carrier system comprises one or more natural or synthetic tocopherols or tocotrienols, or any combinations thereof, in an amount from about 60% to about 75% (w/w). In some embodiments, the carrier system comprises one or more natural or synthetic tocopherols or tocotrienols, or any combinations thereof, in an amount of about 70% (w/w). In some embodiments, a synthetic tocopherol can include Vitamin E TPGS (Vitamin E polyethylene glycol succinate). In some embodiments, on the other hand, synthetic tocopherols exclude tocopherols covalently bonded or linked (e.g. through a diacid linking group) to a glycol polymer, such as polyethylene glycol). Thus, in some embodiments, the compositions described herein exclude Vitamin E TPGS.

In some embodiments, the carrier system comprises one or more alcohols or glycols, or any combinations thereof, in an amount from about 10% to about 55%, about 10% to about 40%, about 10% to about 35%, about 12% to about 55%, about 12% to about 40%, about 12% to about 35%, about 15% to about 55%, about 15% to about 40%, about 15% to about 35%, about 10%, about 12.5%, about 15%, about 17.5%, about 20%, about 22.5%, about 25%, about 27.5%, about 30%, about 32.5%, about 35%, about 37.5%, about 40%, about 42.5%, about 45%, about 47.5%, about 50%, about 52.5% or about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount of about 30% (w/w). In some embodiments, the alcohol is ethanol or contains ethanol. In some preferred embodiments, the glycols exclude glycol polymers.

In some preferred embodiments, the glycols exclude glycol polymers having an average molecular weight of greater than 200. In some embodiments, the glycols exclude polyethylene glycol having an average molecular weight of greater than about 200.

In some embodiments, the carrier system comprises one or more alcohols or glycols, or any combinations thereof, in an amount from about 15% to about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount of about 30% (w/w).

In some embodiments, the composition comprises at least one additional ingredient selected from the group consisting of: active pharmaceutical ingredients; enhancers; excipients; and agents used to adjust the pH, buffer the composition, prevent degradation, and improve appearance, odor, or taste.

In some embodiments, the compositions comprise at least one alkyl glycoside. In some embodiments, the at least one alkyl glycoside is one described in U.S. Pat. No. 5,661,130, which is incorporated by reference herein.

In some embodiments, the composition comprises a benzodiazepine drug that is fully dissolved in a solvent comprising a natural or synthetic tocopherol or tocotrienol, and an alcohol or glycol. In some embodiments, the composition comprises a benzodiazepine drug that is fully dissolved in a solvent comprising a natural or synthetic tocopherol or tocotrienol and an alcohol or glycol, wherein the solution is at least substantially free of water. (In some embodiments, "substantially free of water" indicates that the solution contains less than about 1%, less than about 0.5%, less than about 0.25% or less than about 0.1% water.) In some embodiments, the composition consists essentially of a benzodiazepine drug that is fully dissolved in a solvent consisting of one or more natural or synthetic tocopherols or tocotrienols, one or more alcohols or glycols, and optionally one or more alkyl glycosides. In some embodiments, the composition consists essentially of a benzodiazepine drug that is fully dissolved in a solvent consisting of one or more natural or synthetic tocopherols or tocotrienols, one or more alcohols or glycols, and optionally one or more alkyl glycosides wherein the solution is at least substantially free of water. (In some embodiments, "substantially free of water" indicates that the solution contains less than about 1%, less than about 0.5%, less than about 0.25% or less than about 0.1% water.) In some embodiments, the composition consists of a benzodiazepine dissolved in a solvent consisting of one or more natural or synthetic tocopherols or tocotrienols, one or more alcohols or glycols, and optionally one or more alkyl glycosides. In some embodiments, the composition consists of a benzodiazepine dissolved in a solvent consisting of one or more natural or synthetic tocopherols or tocotrienols, one or more alcohols or glycols, and optionally one or more alkyl glycosides, wherein the solution is at least substantially free of water. (In some embodiments, "substantially free of water" indicates that the solution contains less than about 1%, less than about 0.5%, less than about 0.25% or less than about 0.1% water.)

In some embodiments, the composition comprises a benzodiazepine drug that is fully dissolved in a solvent comprising a natural or synthetic tocopherol or tocotrienol, and an alcohol or glycol. Thus, in some embodiments, the composition is substantially free of benzodiazepine microparticles, nanoparticles or combinations thereof. In some embodiments, the composition comprises a benzodiazepine drug that is fully dissolved in a solvent comprising a natural or synthetic tocopherol or tocotrienol and an alcohol or glycol, wherein the solution is at least substantially free of water. (In some embodiments, "substantially free of water" indicates that the solution contains less than about 1%, less than about 0.5%, less than about 0.25% or less than about 0.1% water.) In some embodiments, the composition consists essentially of a benzodiazepine drug that is fully dissolved in a solvent consisting of one or more natural or synthetic tocopherols or tocotrienols, one or more alcohols or glycols, and optionally one or more alkyl glycosides. In some embodiments, the composition consists essentially of a benzodiazepine drug that is fully dissolved in a solvent consisting of one or more natural or synthetic tocopherols or tocotrienols, one or more alcohols or glycols, and optionally one or more alkyl glycosides wherein the solution is at least substantially free of water. (In some embodiments, "substantially free of water" indicates that the solution contains less than about 1%, less than about 0.5%, less than about 0.25% or less than about 0.1% water.) In some embodiments, the composition consists of a benzodiazepine dissolved in a solvent consisting of one or more natural or synthetic tocopherols, one or more alcohols or glycols, and optionally one or more alkyl glycosides. In some embodiments, the composition consists of a benzodiazepine dissolved in a solvent consisting of one or more natural or synthetic tocopherols, one or more alcohols or glycols, and optionally one or more alkyl glycosides, wherein the solution is at least substantially free of water. (In some embodiments, "substantially free of water" indicates that the solution contains less than about 1%, less than about 0.5%, less than about 0.25% or less than about 0.1% water.)

In some embodiments, the composition contains a benzodiazepine drug that at least partially in a particulate form suspended in a carrier system containing a natural or synthetic tocopherol or tocotrienol and one or more alcohols or glycols. In some embodiments, substantially all the benzodiazepine drug is in a particulate form. In some embodiments, at least part of the benzodiazepine drug is in a microparticulate or nanoparticulate form. The carrier system is one in which the amount of at least one benzodiazepine present in the composition exceeds its solubility in the carrier system. In some embodiments, a carrier system in such a composition includes water. In some embodiments, such a liquid carrier system contains water and one or more excipients. In some embodiments, one or more excipients are dissolved or suspended in the carrier system. In some embodiments, at least one such excipient stabilizes the suspension of benzodiazepine particulates in the carrier system. In some embodiments, the carrier system may contain varying concentrations of parabens (e.g. methylparaben, propylparaben, etc.), and/or varying amounts of one or more surfactants, such as povidone (polyvinyl pyrrolidinone). In some embodiments, benzodiazepine particulate suspensions specifically exclude one or more polymeric glycols, such as polyethylene glycol. In some embodiments, benzodiazepine particulate suspensions specifically exclude one or more polymeric glycols having a molecular weight greater than about 200 g/mol. In some embodiments, the composition comprises a benzodiazepine drug in a form including benzodiazepine microparticles and/or nanoparticles suspended in a carrier system comprising synthetic tocopherol, one or more parabens, one or more alcohols or glycols, one or more surfactants and water. In some embodiments, the composition comprises a benzodiazepine drug in a form including benzodiazepine microparticles or nanoparticles suspended in a carrier system comprising Vitamin E TPGS, one or both of methylparaben and propylparaben, at least one glycol, povidone and water. In some embodiments, the composition comprises a benzodiazepine drug in a form including benzodiazepine microparticles and/or nanoparticles suspended in a carrier system comprising Vitamin E TPGS, methylparaben, propylparaben, propylene glycol, povidone and water. In some embodiments, the composition consists essentially of a benzodiazepine drug in a form including benzodiazepine microparticles and/or nanoparticles suspended in a carrier system consisting essentially of a synthetic tocopherol, one or more parabens, one or more alcohols or glycols, one or more surfactants and water. In some embodiments, the composition consists essentially of a benzodiazepine drug in a form including benzodiazepine microparticles or nanoparticles suspended in a carrier system consisting essentially of Vitamin E TPGS, one or both of methylparaben and propylparaben, at least one glycol, povidone and water. In some embodiments, the composition consists essentially of a benzodiazepine drug in a form including benzodiazepine microparticles and/or nanoparticles suspended in a carrier system consisting essentially of Vitamin E TPGS, methylparaben, propylparaben, propylene glycol, povidone and water. In some embodiments, the composition consists of a benzodiazepine drug in a form including benzodiazepine microparticles and/or nanoparticles suspended in a carrier system consisting of a synthetic tocopherol, one or more parabens, one or more alcohols or glycols, one or more surfactants and water. In some embodiments, the composition consists of a benzodiazepine drug in a form including benzodiazepine microparticles or nanoparticles suspended in a carrier system consisting of Vitamin E TPGS, one or both of methylparaben and propylparaben, at least one glycol, povidone and water. In some embodiments, the composition consists of a benzodiazepine drug in a form including benzodiazepine microparticles and/or nanoparticles suspended in a carrier system consisting of Vitamin E TPGS, methylparaben, propylparaben, propylene glycol, povidone and water.

In some embodiments, the composition contains a benzodiazepine drug that at least partially in a particulate form suspended in a carrier system containing a natural or synthetic tocopherol or tocotrienol, one or more alcohols or glycols, and an alkyl glycoside. In some embodiments, substantially all the benzodiazepine drug is in a particulate form. In some embodiments, at least part of the benzodiazepine drug is in a microparticulate or nanoparticulate form. The carrier system is one in which the amount of at least one benzodiazepine present in the composition exceeds its solubility in the carrier system. In some embodiments, a carrier system in such a composition includes water. In some embodiments, such a liquid carrier system contains water and one or more excipients. In some embodiments, one or more excipients are dissolved or suspended in the carrier system. In some embodiments, at least one such excipient stabilizes the suspension of benzodiazepine particulates in the carrier system. In some embodiments, the carrier system may contain varying concentrations of parabens (e.g. methylparaben, propylparaben, etc.), and/or varying amounts of one or more surfactants, such as povidone (polyvinyl pyrrolidinone). In some embodiments, benzodiazepine particulate suspensions specifically exclude one or more polymeric glycols, such as polyethylene glycol. In some embodiments, benzodiazepine particulate suspensions specifically exclude one or more polymeric glycols having a molecular weight greater than about 200 g/mol. In some embodiments, the composition comprises a benzodiazepine drug in a form including benzodiazepine microparticles and/or nanoparticles suspended in a carrier system comprising a synthetic tocopherol, one or more parabens, one or more alcohols or glycols, an alkyglycoside and water. In some embodiments, the composition comprises a benzodiazepine drug in a form including benzodiazepine microparticles or nanoparticles suspended in a carrier system comprising Vitamin E TPGS, one or both of methylparaben and propylparaben, at least one glycol, an alkyl glycoside and water. In some embodiments, the composition comprises a benzodiazepine drug in a form including benzodiazepine microparticles and/or nanoparticles suspended in a carrier system comprising Vitamin E TPGS, methylparaben, propylparaben, propylene glycol, an alkyl glycoside and water. In some embodiments, the composition consists essentially of a benzodiazepine drug in a form including benzodiazepine microparticles and/or nanoparticles suspended in a carrier system consisting essentially of a synthetic tocopherol, one or more parabens, one or more alcohols or glycols, an alkyl glycoside, optionally a surfactant, and water. In some embodiments, the composition consists essentially of a benzodiazepine drug in a form including benzodiazepine microparticles or nanoparticles suspended in a carrier system consisting essentially of Vitamin E TPGS, one or both of methylparaben and propylparaben, at least one glycol, an alkyl glycoside, optionally a povidone and water. In some embodiments, the composition consists essentially of a benzodiazepine drug in a form including benzodiazepine microparticles and/or nanoparticles suspended in a carrier system consisting essentially of Vitamin E TPGS, methylparaben, propylparaben, propylene glycol, an alkyl glycoside, optionally a povidone, and water. In some embodiments, the composition consists of a benzodiazepine drug in a form including benzodiazepine microparticles and/or nanoparticles suspended in a carrier system consisting of a synthetic tocopherol, one or more parabens, one or more alcohols or glycols, an alkyl glycoside, optionally one or more surfactants, and water. In some embodiments, the composition consists of a benzodiazepine drug in a form including benzodiazepine microparticles or nanoparticles suspended in a carrier system consisting of Vitamin E TPGS, one or both of methylparaben and propylparaben, at least one glycol, an alkyl glycoside, optionally a povidone and water. In some embodiments, the composition consists of a benzodiazepine drug in a form including benzodiazepine microparticles and/or nanoparticles suspended in a carrier system consisting of Vitamin E TPGS, methylparaben, propylparaben, propylene glycol, an alkyl glycoside, optionally a povidone and water.

The invention also discloses a method of treating a patient with a disorder that may be treatable with a benzodiazepine drug. In some embodiments, the patient is a human. In some embodiments, the method comprises: administering to one or more nasal mucosal membranes of a patient a pharmaceutical composition for nasal administration comprising a benzodiazepine drug; one or more natural or synthetic tocopherols or tocotrienols, or any combinations thereof, in an amount from about 30% to about 95% (w/w); and one or more alcohols or glycols, or any combinations thereof, in an amount from about 5% to about 70% (w/w), preferably about 10% to about 70% (w/w). In some embodiments, the benzodiazepine is dissolved in the one or more natural or synthetic tocopherols or tocotrienols, or any combinations thereof, in an amount from about 30% to about 95% (w/w); and the one or more alcohols or glycols, or any combinations thereof, in an amount from about 5% to about 70% (w/w), preferably about 10% to about 70% (w/w). In some embodiments, the benzodiazepine drug is dissolved in a carrier system. In other embodiments, at least part of the benzodiazepine drug is in a form including microparticles, nanoparticles, or combinations thereof. In some embodiments, the composition is substantially free of benzodiazepine microparticles, nanoparticles or combinations thereof.

In some embodiments, the benzodiazepine drug is selected from the group consisting of alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, or any pharmaceutically-acceptable salts thereof, and any combinations thereof. In some embodiments, the benzodiazepine drug is diazepam, or a pharmaceutically-acceptable salt thereof. In some embodiments, the benzodiazepine drug comprises benzodiazepine microparticles, nanoparticles, or combinations thereof. In some embodiments, the benzodiazepine nanoparticles have an effective average particle size of less than about 5000 nm.

In some embodiments, the one or more natural or synthetic tocopherols or tocotrienols are selected from the group consisting of α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof. A synthetic tocopherol may include a tocopherol that has been modified to include a hydrophilic group, such as a polyethylene glycol group, which may be directly covalently bonded to the tocopherol or may be linked to the tocopherol through a covalent linking group, such as a diacid. An exemplary synthetic tocopherol of this type is Vitamin E Polyethylene Glycol Succinate (Vitamin E TPGS), although the person skilled in the art will be able to envision other synthetic tocopherols that have similar diacid and/or hydrophilic groups.

In some embodiments, the one or more alcohols are selected from the group consisting of: ethanol, propyl alcohol, butyl alcohol, pentanol, benzyl alcohol, any isomers thereof, and any combinations thereof. In some embodiments, the one or more glycols are selected from the group consisting of ethylene glycol, propylene glycol, butylene glycol, pentylene glycol, any isomers thereof, and any combinations thereof. In some embodiments, one or more glycols specifically excludes polymeric glycols, such as polyethylene glycol. In some embodiments, one or more glycols specifically excludes a polymeric glycol having a molecular weight of greater than about 200 g/mol.

In some embodiments, the benzodiazepine drug is present in the carrier system in a concentration from about 1 mg/mL to about 600 mg/mL. In some embodiments, the benzodiazepine drug is present in the carrier system in a concentration of from about 10 mg/mL to about 250 mg/mL. In some embodiments, the benzodiazepine drug is present in the carrier system in a concentration of from about 20 mg/mL to about 50 mg/mL.

In some embodiments, the carrier system comprises one or more natural or synthetic tocopherols or tocotrienols, or any combinations thereof, in an amount from about 45% to about 85% (w/w). In some embodiments, the carrier system comprises one or more natural or synthetic tocopherols or tocotrienols, or any combinations thereof, in an amount from about 60% to about 75% (w/w). In some embodiments, the carrier system comprises one or more natural or synthetic tocopherols or tocotrienols, or any combinations thereof, in an amount of about 70% (w/w). In some embodiments, especially where particulate suspensions of a benzodiazepine drug are contemplated, the compositions may include a tocopherol, especially a synthetic tocopherol having a hydrophilic group covalently linked to a tocopherol. In other embodiments, especially where a solution of benzodiazepine drug is contemplated, the tocopherol is substantially or completely free of Vitamin E TPGS.

In some embodiments, the carrier system comprises one or more alcohols or glycols, or any combinations thereof, in an amount from about 10% to about 55% (w/w). In some embodiments, the carrier system comprises one or more alcohols or glycols, or any combinations thereof, in an amount from about 25% to about 40% (w/w). In some embodiments, the carrier system comprises one or more alcohols or glycols, or any combinations thereof, in an amount from about 30% (w/w). In some embodiments the amount of one or more alcohols or glycols in the carrier system is about 10% to about 55%, about 10% to about 40%, about 10% to about 35%, about 12% to about 55%, about 12% to about 40%, about 12% to about 35%, about 15% to about 55%, about 15% to about 40%, about 15% to about 35%, about 10%, about 12.5%, about 15%, about 17.5%, about 20%, about 22.5%, about 25%, about 27.5%, about 30%, about 32.5%, about 35%, about 37.5%, about 40%, about 42.5%, about 45%, about 47.5%, about 50%, about 52.5% or about 55% (w/w).

In some embodiments, the composition comprises at least one additional ingredient selected from the group consisting of: active pharmaceutical ingredients; enhancers; excipients; and agents used to adjust the pH, buffer the composition, prevent degradation, and improve appearance, odor, or taste.

In some embodiments, a composition comprises at least one penetration enhancer in addition to a benzodiazepine drug, a natural or synthetic tocopherol or tocotrienol, and an alcohol or glycol. In some embodiments, the penetration enhancer is an alkyl glycoside. In some embodiments, the alkyl glycoside refers to any sugar joined to any hydrophobic alkyl, as described in U.S. Pat. No. 5,661,130, which is incorporated herein by reference in its entirety. The hydrophobic alkyl can be any suitable length, for example about 9 to about 24 carbons in length, especially about 10 to about 14 carbons in length. The hydrophobic alkyl can be branched and/or partially or wholly unsaturated. The alkyl may be joined to the saccharide core for example through a carbonyl group, whereby an ester group may be formed. A suitable alkyl glycoside will have the characteristics of being nontoxic, nonionic, and capable of increasing the absorption of a benzodiazepine drug when it is administered intranasally as described herein. Exemplary saccharides that may be covalently joined to an alkyl according to the present invention include glucose, maltose, maltotriose, maltotetrose, sucrose and trehalose. Exemplary alkyl glycosides that may be employed include octyl-, nonyl-, decyl-, undecyl-, dodecyl, tridecyl, tetradecyl, pentadecyl, octadecyl α- or β-D-maltoside, -glucoside or sucroside. In some embodiments, the preferred glycosides include maltose, sucrose or glucose linked by glycosidic linkage to an alkyl chain of 9, 10, 12, 14, 16, 18 or 20 carbon atoms. Where present, the amount of alkyl glycoside in the composition is sufficient to enhance the absorption of a benzodiazepine drug administered by the intranasal route. In some embodiments, the amount of alkyl glycoside in the composition is selected so as to enhance absorption of the benzodiazepine drug, while at the same time not significantly irritating the nasal mucosa. In some embodiments, the amount of alkyl glycoside in the composition is in a range of about 0.01% (w/v) to about 1% (w/v). In some embodiments, the amount of alkyl glycoside in the composition is in a range of about 0.05% (w/v) to about 0.5% (w/v), or about 0.125% (w/v) to about 0.5% (w/v).

In some embodiments, the composition is in a pharmaceutically-acceptable spray formulation, and further comprising administering the composition to one or more nasal mucosal membranes of the patient. In some embodiments, the therapeutically effective amount is from about 1 mg to about 20 mg of the benzodiazepine. In some embodiments, the pharmaceutical composition is in a pharmaceutically-acceptable spray formulation having volume from about 10 μL to 200 μL.

In some embodiments, the administration of the composition comprises spraying at least a portion of the therapeutically effective amount of the composition into at least one nostril. In some embodiments, the administration of the composition comprises spraying at least a portion of the therapeutically effective amount of the composition into each nostril. In some embodiments, the administration of the composition comprises spraying a first quantity of the composition into the first nostril, spraying a second quantity of the composition into a second nostril, and optionally after a pre-selected time delay, spraying a third quantity of the composition into the first nostril. Some embodiments further comprise, optionally after a pre-selected time delay, administering at least a fourth quantity of the composition to the second nostril.

In some embodiments, the administration of the composition begins at any time before or after onset of symptoms of a disorder which may be treatable with the composition.

Definitions

As used herein the phrase "therapeutically effective amount" (or more simply "effective amount") includes an amount sufficient to provide a specific therapeutic response for which the drug is administered to a patient in need of particular treatment. The skilled clinician will recognize that the therapeutically effective amount of drug will depend upon the patient, the indication and the particular drug administered.

As used herein, the modifier "about" is intended to have its regularly recognized meaning of approximately. In some embodiments, the term may be more precisely interpreted as meaning within a particular percentage of the modified value, e.g. "about" may in some embodiments mean±20%, ±10%, ±5%, ±2%, or ±1% or less.

As used herein, the phrase "analogs or derivatives" includes molecules that differ from one another molecule due to one or more atoms or functional groups having been replaced with a different atom or functional group. This may result in molecules with similar chemical formulas but different chemical and/or biological properties.

As used herein, the term, "isomer" includes molecules with identical chemical formulas, but between which the arrangement of the molecules may vary. These varying arrangements may result in molecules with identical chemical formulas but different chemical properties. By way of non-limiting example, propanol has the chemical formula $C_3H_7OH$. It may be found as propan-1-ol, wherein the —OH is found attached to an end carbon. Alternatively, it may be found as propan-2-ol, wherein the —OH is found attached to the second carbon.

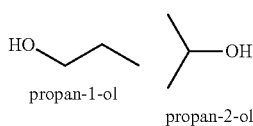

propan-1-ol propan-2-ol

As used herein, the term "seizure" includes commonly recognized types of seizures, including absence seizures, myoclonic seizures, clonic seizures, tonic seizures, tonic-clonic seizures, and atonic seizures. Often seizures, particularly severe tonic or tonic-clonic seizures, will be presaged by one or more aura that will be familiar to the patient or those familiar with the patient. Each patient will generally experience a different type of aura, which is unique to the patient; however auras may be classified as audible, visual, olfactory or tactile sensations that usually, or at least often, precedes a patient's experiencing a seizure. (Not all patients who suffer seizures experience aura; however aura are not uncommon amongst those who suffer the worst type of seizures, especially tonic-clonic seizures.)

As used herein, the term "prevention" refers to a forestalling, including temporary forestalling, of the onset of a disorder. In the case of seizures, this can occur either with or without the benefit of a warning aura.

As used herein, the term "treatment" refers to a reduction in the intensity and/or duration of a disorder, or similar effects. The term also encompasses the side-effects of such a "treatment."

As used herein, unless otherwise qualified, "a" and "an" can mean one or more.

As used herein, the term "comprising" in all its variants, is a transitional phrase used in a claim to indicate that the invention includes or contains, but is not limited to, the specifically recited claim elements.

As used herein, the phrase "consisting essentially of" is a transitional phrase used in a claim to indicate that the a following list of ingredients, parts or process steps must be present in the claimed composition, machine or process, but that the claim is open to unlisted ingredients, parts or process steps that do not materially affect the basic and novel properties of the invention.

As used herein, the term "consisting of" is a transitional phrase used in a claim to indicate that the claimed invention includes only those elements set forth in the claim.

Benzodiazepine Drugs

In the context of the present invention, the term "benzodiazepine drug" includes any therapeutically effective benzodiazepine compound, or pharmaceutically acceptable salt, or combinations thereof. In some embodiments, benzodiazepine comprises a member of the group consisting of alprazolam, diazepam, flurazepam, lorazepam, medazepam, mexazolam, midazolam, temazepam and pharmaceutically acceptable salts and combinations thereof.

It should be recognized by those of skill in the art that additional benzodiazepine compounds that have heretofore been considered to have marginal or little therapeutic benefit, either because of low bioavailability, poor pharmacokinetic properties or poor pharmacodynamic properties, may find use through the present invention, which can provide for improved bioavailability of benzodiazepine drugs, delivery of higher concentrations of benzodiazepine drugs via the nasal route, faster attainment of therapeutic levels of benzodiazepine in the blood plasma, avoidance of the liver portal vein and concomitant avoidance of first pass effects and/or faster presentation of benzodiazepine drug to the brain.

For example, most benzodiazepines are so slightly soluble in water that a therapeutically effective amount cannot be dissolved in a volume of aqueous solvent that is amenable to application to a mucosal membrane. By use of the present carrier system, which in some embodiments, provides an improved ability to dissolve benzodiazepine drugs, the present invention allows benzodiazepine drugs to be administered to one or more mucosal membranes, including to nasal mucosal membranes. This can allow one to administer the drug without hospitalization or unnecessary discomfort. Additionally, in some embodiments of the present invention, such as nasal administration, the digestive system largely may be bypassed. This latter improvement can yield improved bioavailability, faster attainment of therapeutic levels of benzodiazepine in the blood plasma, avoidance of the liver portal vein, and/or concomitant avoidance of first pass effects.

Nasal administration of the composition can result in faster presentation of the one or more benzodiazepine drugs to the brain due to the close proximity of the membranes and the brain. A seizing patient, for example, suffers from rigid muscles and uncontrollable movement. This can make oral and/or intravenous administration difficult or inconvenient. However, the nasal passageways remain open and easily accessible, and therefore is a useful route of administration for of the present invention.

In some embodiments, the pharmaceutical composition is used to treat a patient suffering from a disorder that is amenable to treatment or prevention with an effective amount of the one or more benzodiazepine drugs. By way of non-limiting example such disorders can include: insomnia, anxiety, seizures, muscle spasms and rigidity, and the symptoms of drug withdrawal.

In some embodiments, the one or more benzodiazepine drugs, are used alone or in combination with another anticonvulsant drug to treat seizure, protect against seizure, reduce or ameliorate the intensity of seizure, reduce or ameliorate the frequency of seizure, and/or prevent occurrence or re-occurrence of seizure.

Alprazolam (8-chloro-6-phenyl-1-methyl-4H-1,2,4-triazolo[4,3-a][1,4]benzodiazepine)

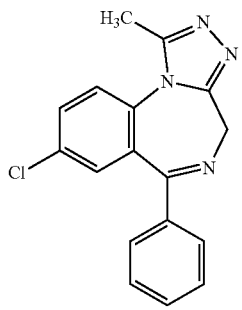 [SMILES: Cc1nnc2n1-c1ccc(Cl)cc1C(c1ccccc1)=NC2]

Alprazolam is a benzodiazepine drug having sedative, tranquilizing and muscle relaxing properties. It is classified as an anxiolytic. Alprazolam has also been shown to be useful in the treatment of panic disorder. The dosage of alprazolam varies by indication, however it is expected that a therapeutic dose will be in the range of about 0.5 to about 4, preferably about 1 to about 2 mg per dose, from 1 to 8, preferably from 2 to 8, and in some preferred embodiments about 4 to about 6 times per day. Alprazolam may be manufactured using the process disclosed in U.S. Pat. No. 3,987,052, which is incorporated herein by reference in its entirety.

In some embodiments, alprazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, alprazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Alprazolam may be administered by the patient or other person (such as a healthcare professional) while the patient is in a non-seizing state to protect against seizure. Even where protection against seizure is not absolute, administration of alprazolam may reduce or ameliorate the intensity of seizure and/or reduce or ameliorate the frequency of seizure. In some embodiments, administration of alprazolam may prevent occurrence of seizure. In some embodiments, especially where the patient is prone to experiencing serial seizures or status epilepticus, administration of alprazolam may aid in interrupting the seizure cycle and may thus prevent the re-occurrence of seizure. In addition to the benzodiazepines (such as diazepam), other anti-convulsant drugs may be combined with alprazolam to provide an anticonvulsant or synergistic anticonvulsant effect.

Alprazolam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the alprazolam formulations of the invention, and in particular nasal formulations, provide fast onset of therapeutic benefit—in some instances less than about 30 minutes, less than about 15 minutes, less than about 10 minutes, and in some cases less than about 5 minutes. The alprazolam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Diazepam (7-chloro-1-methyl-5-phenyl-1,3-dihydro-2H-1,4-benzodiazepin-2-one)

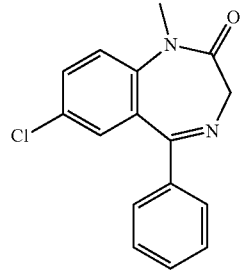 [SMILES: CN1C(=O)CN=C(c2ccccc2)c2cc(Cl)ccc21]

Diazepam is a benzodiazepine drug having sedative, tranquilizing and muscle relaxing properties. It is classified as an anxiolytic and skeletal muscle relaxant. It possesses anxiolytic, anticonvulsant, sedative, skeletal muscle relaxant and amnesic properties. The dosage of diazepam may vary by indication, however it is expected that a therapeutic dose will be in the range of about 1 to about 20, preferably about 2 to about 10 mg per dose, from 1 to 8, preferably from 2 to 8, and in some preferred embodiments about 4 to about 6 times per day. Diazepam may be manufactured using the process disclosed in one of U.S. Pat. Nos. 3,371,085; 3,109,843; 3,136,815 or 3,102,116, each of which is incorporated herein by reference in its entirety.

In some embodiments, diazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, diazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Diazepam may be administered by the patient or other person (such as a healthcare professional) while the patient is in a non-seizing state to protect against seizure. Even where protection against seizure is not absolute, administration of diazepam may reduce or ameliorate the intensity of seizure and/or reduce or ameliorate the frequency of seizure. In some embodiments, administration of diazepam may prevent occurrence of seizure. In some embodiments, especially where the patient is prone to experiencing serial seizures or status epilepticus, administration of diazepam may aid in interrupting the seizure cycle and may thus prevent the re-occurrence of seizure. In addition to the benzodiazepines (such as diazepam), other anti-convulsant drugs may be combined with diazepam to provide a synergistic anticonvulsant effect.

Diazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the diazepam formulations of the invention, and in particular nasal formulations, provide fast onset of therapeutic benefit—in some instances less than about 30 minutes, less than about 15 minutes, less than about 10 minutes, and in some cases less than about 5 minutes. The diazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Flurazepam (7-chloro-5-(2-fluorophenyl)-2,3-dihydro-1-(2-(diethylamino)ethyl)-1H-1,4-benzodiazepin-2-one)

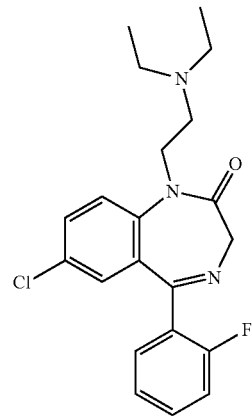 [SMILES: CCN(CC)CCN1C(=O)CN=C(c2ccccc2F)c2cc(Cl)ccc21]

Flurazepam is a benzodiazepine drug having sedative (especially soporific and hypnotic), anxiolytic, anticonvulsant and muscle relaxing properties. It is classified as an sedative, hypnotic. Flurazepam has been shown to be useful in the treatment of insomnia. The dosage of flurazepam varies by indication, however it is expected that a therapeutic dose will be in the range of about 5 to 40, preferably about 20 to about 35 mg per dose, from 1 to 8, preferably from 2 to 8, and in some preferred embodiments about 4 to about 6 times per day. Flurazepam may be manufactured using the process disclosed in U.S. Pat. Nos. 3,567,710 or 3,299,053, each of which is incorporated herein by reference in its entirety.

In some embodiments, flurazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, flurazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Flurazepam may be administered by the patient or other person (such as a healthcare professional) while the patient is in a non-seizing state to protect against seizure. Even where protection against seizure is not absolute, administration of flurazepam may reduce or ameliorate the intensity of seizure and/or reduce or ameliorate the frequency of seizure. In some embodiments, administration of flurazepam may prevent occurrence of seizure. In some embodiments, especially where the patient is prone to experiencing serial seizures or status epilepticus, administration of flurazepam may aid in interrupting the seizure cycle and may thus prevent the re-occurrence of seizure. In addition to the benzodiazepines (such as diazepam), other anti-convulsant drugs may be combined with flurazepam to provide a synergistic anticonvulsant effect.

Flurazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the flurazepam formulations of the invention, and in particular nasal formulations, provide fast onset of therapeutic benefit—in some instances less than about 30 minutes, less than about 15 minutes, less than about 10 minutes, and in some cases less than about 5 minutes. The flurazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Lorazepam (7-chloro-5-(2-chlorophenyl)-3-hydroxy-1,3-dihydro-2H-1,4-benzodiazepin-2-one)

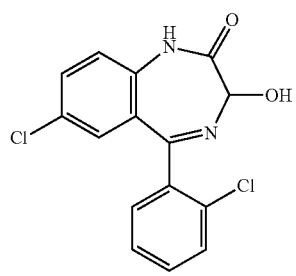 [SMILES: O=C1Nc2ccc(Cl)cc2C(c2ccccc2Cl)=NC1O]

Lorazepam is a benzodiazepine drug having sedative, tranquilizing, anticonvulsant, amnesic and muscle relaxing properties. It is classified as an anxiolytic. Lorazepam has also been shown to be useful in the treatment of nausea. The dosage of lorazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Lorazepam may be manufactured using the process disclosed in U.S. Pat. No. 3,296,249, which is incorporated herein by reference in its entirety.

In some embodiments, lorazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, lorazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Lorazepam may be administered by the patient or other person (such as a healthcare professional) while the patient is in a non-seizing state to protect against seizure. Even where protection against seizure is not absolute, administration of lorazepam may reduce or ameliorate the intensity of seizure and/or reduce or ameliorate the frequency of seizure. In some embodiments, administration of lorazepam may prevent occurrence of seizure. In some embodiments, especially where the patient is prone to experiencing serial seizures or status epilepticus, administration of lorazepam may aid in interrupting the seizure cycle and may thus prevent the re-occurrence of seizure. In addition to the benzodiazepines (such as diazepam), other anti-convulsant drugs may be combined with lorazepam to provide a synergistic anticonvulsant effect.

Lorazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the lorazepam formulations of the invention, and in particular nasal formulations, provide fast onset of therapeutic benefit—in some instances less than about 30 minutes, less than about 15 minutes, less than about 10 minutes, and in some cases less than about 5 minutes. The lorazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Medazepam ((7-chloro-1-methyl-5-phenyl-2,3-dihydro-1H-1,4-benzodiazepine)

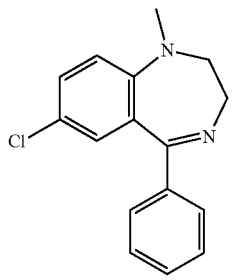 [SMILES: CN1CCN=C(c2ccccc2)c2cc(Cl)ccc21]

Medazepam is a benzodiazepine drug having sedative, tranquilizing, anticonvulsant, amnesic and muscle relaxing properties. It is classified as an anxiolytic. Medazepam has also been shown to be useful in the treatment of nausea. The dosage of medazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Medazepam may be manufactured using the process disclosed in U.S. Pat. No. 3,243,427, which is incorporated herein by reference in its entirety.

In some embodiments, medazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, medazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Medazepam may be administered by the patient or other person (such as a healthcare professional) while the patient is in a non-seizing state to protect against seizure. Even where protection against seizure is not absolute, administration of medazepam may reduce or ameliorate the intensity of seizure and/or reduce or ameliorate the frequency of seizure. In some embodiments, administration of medazepam may prevent occurrence of seizure. In some embodiments, especially where the patient is prone to experiencing serial seizures or status epilepticus, administration of medazepam may aid in interrupting the seizure cycle and may thus prevent the reoccurrence of seizure. In addition to the benzodiazepines (such as diazepam), other anti-convulsant drugs may be combined with medazepam to provide a synergistic anticonvulsant effect.

Medazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the medazepam formulations of the invention, and in particular nasal formulations, provide fast onset of therapeutic benefit—in some instances less than about 30 minutes, less than about 15 minutes, less than about 10 minutes, and in some cases less than about 5 minutes. The medazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Mexazolam (10-Chloro-11b-(2-chlorophenyl)-1,3,7,11b-tetrahydro-3-methyloxazolo [3,2-d][1,4]benzodiazepin-6(5H)-one)

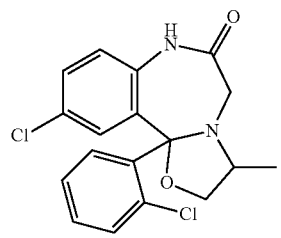 [SMILES: CC1COC2(c3ccccc3Cl)c3cc(Cl)ccc3NC(=O)CN12]

Mexazolam is a benzodiazepine drug having sedative, tranquilizing, anticonvulsant, amnesic and muscle relaxing properties. It is classified as an anxiolytic. Mexazolam has also been shown to be useful in the treatment of nausea. The dosage of mexazolam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Mexazolam may be manufactured using the process disclosed in U.S. Pat. No. 3,722,371, which is incorporated herein by reference in its entirety.

In some embodiments, mexazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, mexazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Mexazolam may be administered by the patient or other person (such as a healthcare professional) while the patient is in a non-seizing state to protect against seizure. Even where protection against seizure is not absolute, administration of mexazolam may reduce or ameliorate the intensity of seizure and/or reduce or ameliorate the frequency of seizure. In some embodiments, administration of mexazolam may prevent occurrence of seizure. In some embodiments, especially where the patient is prone to experiencing serial seizures or status epilepticus, administration of mexazolam may aid in interrupting the seizure cycle and may thus prevent the re-occurrence of seizure. In addition to the benzodiazepines (such as diazepam), other anti-convulsant drugs may be combined with mexazolam to provide a synergistic anticonvulsant effect.

Mexazolam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the mexazolam formulations of the invention, and in particular nasal formulations, provide fast onset of therapeutic benefit—in some instances less than about 30 minutes, less than about 15 minutes, less than about 10 minutes, and in some cases less than about 5 minutes. The mexazolam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Midazolam (8-chloro-6-(2-fluorophenyl)-1-methyl-4H-imidazo(1,5-a)benzodiazepine)

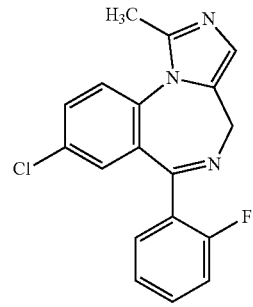 [SMILES: Cc1ncc2n1-c1ccc(Cl)cc1C(c1ccccc1F)=NC2]

Midazolam is a tricyclic benzodiazepine having anxiolytic, amnesic, hypnotic, anticonvulsant, skeletal muscle relaxant and sedative properties. Midazolam is considered soluble in water at a pH lower than about 4, but is relatively insoluble in most aqueous solutions at neutral pH (e.g. about 6 to 8). Thus it is desirable in some embodiments for aqueous nasal preparations of midazolam to have a pH above about 5.5, preferably above about 6.0, or above about 6.5. In some preferred embodiments, the pH is between about 6 and 9, between about 6 and 8. It is considered that preparations of midazolam are particularly suitable for nasal administration as the lipid-soluble (at approximately neutral pH) midazolam is rapidly absorbed across nasal mucosa, leading to efficient uptake of midazolam. It is further considered that midazolam may be formulated in a non-aqueous delivery vehicle, such as is known in the aerosol administration art, such as hydrofluorocarbon propellants, hydrocarbon propellants, etc.

The dosage of midazolam varies by indication, however it is expected that a therapeutic dose will be in the range of about 0.1 to about 20, preferably about 0.2 to about 10 mg per dose, from 1 to 8, preferably from 2 to 8, and in some preferred embodiments about 4 to about 6 times per day. Midazolam may be manufactured using the process disclosed in one of U.S. Pat. Nos. 4,280,957 or 5,831,089, each of which is incorporated herein by reference in its entirety.

In some embodiments, midazolam is used alone or in combination with other drugs to provide an anxiolytic effect, an anticonvulsant effect, a sedative effect, a skeletal muscle relaxant effect, an amnesic effect or combinations of the foregoing effects.

In some embodiments, midazolam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Midazolam may be administered by the patient or other person (such as a healthcare professional) while the patient is in a non-seizing state to protect against seizure. Even where protection against seizure is not absolute, administration of midazolam may reduce or ameliorate the intensity of seizure and/or reduce or ameliorate the frequency of seizure. In some embodiments, administration of midazolam may prevent occurrence of seizure. In some embodiments, especially where the patient is prone to experiencing serial seizures or status epilepticus, administration of midazolam may aid in interrupting the seizure cycle and may thus prevent the re-occurrence of seizure. In addition to the benzodiazepines (such as diazepam), other anti-convulsant drugs may be combined with midazolam to provide a synergistic anticonvulsant effect.

Midazolam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the midazolam formulations of the invention, and in particular nasal formulations, provide fast onset of therapeutic benefit—in some instances less than about 30 minutes, less than about 15 minutes, less than about 10 minutes, and in some cases less than about 5 minutes. The midazolam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Temazepam (7-chloro-1-methyl-5-phenyl-3-hydroxy-1,3-dihydro-2H-1,4-benzodiazepin-2-one)

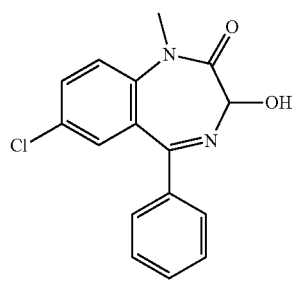 [SMILES: CN1C(=O)C(O)N=C(c2ccccc2)c2cc(Cl)ccc21]

Temazepam is a benzodiazepine drug having sedative, tranquilizing, anticonvulsant, amnesic and muscle relaxing properties. It is classified as an anxiolytic. Temazepam has also been shown to be useful in the treatment of nausea. The dosage of temazepam varies by indication, however it is expected that a therapeutic dose will be in the range of about 1 to about 50, preferably about 5 to about 30 mg per dose, from 1 to 8, preferably from 2 to 8, and in some preferred embodiments about 4 to about 6 times per day. Temazepam may be manufactured using the process disclosed in U.S. Pat. Nos. 3,340,253 or 3,374,225, each of which is incorporated herein by reference in its entirety.

In some embodiments, temazepam is used alone or in combination with other drugs to provide an anxiolytic effect, an anticonvulsant effect, a sedative effect, a skeletal muscle relaxant effect, an amnesic effect or combinations of the foregoing effects.

In some embodiments, temazepam is used alone or in combination with another anticonvulsant drug to treat seizure, protect against seizure, reduce or ameliorate the intensity of seizure, reduce or ameliorate the frequency of seizure, and/or prevent occurrence or re-occurrence of seizure. Temazepam may be administered by the patient or other person (such as a healthcare professional) while the patient is in a non-seizing state to protect against seizure. Even where protection against seizure is not absolute, administration of temazepam may reduce or ameliorate the intensity of seizure and/or reduce or ameliorate the frequency of seizure. In some embodiments, administration of temazepam may prevent occurrence of seizure. In some embodiments, especially where the patient is prone to experiencing serial seizures or status epilepticus, administration of temazepam may aid in interrupting the seizure cycle and may thus prevent the re-occurrence of seizure. In addition to the benzodiazepines (such as diazepam), other anti-convulsant drugs may be combined with temazepam to provide a synergistic anticonvulsant effect.

Temazepam may also be administered by another person (e.g. an acquaintance or associate, a family member or a health care professional) to the patient while the patient is in a state of seizure. Thus, one of the advantages of the formulations according to the present invention is the ability to administer them in an acute therapeutic environment to treat the seizure victim, for example, nasally. Among the beneficial therapeutic effects that may be imparted by acute dosing of benzodiazepine anticonvulsants, such as nasal dosing, are: reduction in the severity of the seizure (e.g. general relaxation of the muscles, reduction in seizure-induced anxiety experienced by the patient and a general impartation of a feeling of well-being to the patient), reduction in the duration of the seizure, reduction in the probability that the patient will experience a repeat seizure, an increase in the interval between the current seizure and the next seizure. Thus, the temazepam formulations of the invention, and in particular nasal formulations, provide fast onset of therapeutic benefit—in some instances less than about 30 minutes, less than about 15 minutes, less than about 10 minutes, and in some cases less than about 5 minutes. The temazepam formulations of the invention, and in particular nasal formulations, also provide convenient administration of a therapeutically beneficial drug to a patient that does not require intravenous drug administration or rectal drug administration.

Often seizures, particularly severe tonic or tonic-clonic seizures, will be presaged by one or more aura events that will be familiar to the patient or those familiar with the patient. These auras are practically sui generis for each patient, but may be classified as audible, visual, olfactory or tactile sensations that usually, or typically, precedes a patient's experiencing a seizure. In some embodiments of the invention, the method includes prompt administration of a preparation of a benzodiazepine drug according to the invention during the aura. In some embodiments, such intra-aural administration of benzodiazepine drug, for example by nasal administration, will prevent or at least ameliorate the effects (intensity, duration or both) of the impending seizure. Thus, in the context of this invention, prevention of seizure refers to a temporary forestalling of the onset of seizure, either with or without the benefit of a warning aura.

Pharmaceutically Acceptable Salts

Benzodiazepines have the generally basic structure of formula I:

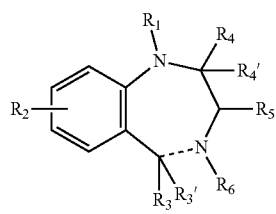

Formula I wherein $R_1$-$R_5$ are substituents. In particular embodiments, $R_1$ is an optionally substituted alkyl or forms a ring with $R_4$, $R_2$ is a halogen (e.g. Cl, Br), $R_3$ is optionally substituted aryl (e.g. 2-Chloro or 2-Fluorophenyl), $R_5$ is H or OH, $R_4$ and $R_4'$ together form a carbonyl (C=O) with the carbon to which they are attached or $R_4$ and $R_1$ form an optionally substituted heterocyclic ring with the diazepam ring atoms to which they are respectively attached; $R_3'$ and $R_6$ together form a double bond or may be combined to form an optionally substituted heterocyclic ring along with the diazepam ring atoms to which they are respectively attached. Such basic compounds may form acid addition salts with pharmaceutically acceptable acids, such as pharmaceutically acceptable mineral acids and pharmaceutically acceptable organic acids.

Pharmaceutically acceptable mineral acids include HCl, $H_2SO_4$, $H_2SO_3$, $H_3PO_4$, $H_3PO_3$, and others that will be recognized by those of skill in the art. Pharmaceutically acceptable organic acids include acetic acid, benzoic acid, tartaric acid, citric acid, oxalic acid, maleic acid, malonic acid, etc. Thus, in some embodiments, the pharmaceutically acceptable acid may be selected from the group consisting of: 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acidascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acidfumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, benzenesulfonic acid (besylic acid), naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p) and undecylenic acid. Other pharmaceutically acceptable acids may be pharmaceutically acceptable acidic (anionic) polymers or pharmaceutically acceptable amphoteric polymers. One skilled in the art will recognize that other basic active pharmaceutical ingredients may be combined with the foregoing acids to produce acid addition salts. Likewise the person skilled in the art will recognize that in some embodiments it may be advantageous that some or all of the added acid be an active pharmaceutical ingredient in its own right.

In some embodiments, the invention provides nasal compositions comprising one or more acidic pharmaceutically active ingredients. It is considered well within the ordinary skill in the art to determine which of the compounds set for the above are acidic. Such compounds may be prepared as base addition salts, e.g. by the addition of one or more mineral bases (e.g. NaOH, KOH, $NaHCO_3$, $Na_2CO_3$, $NH_3$) or organic bases. It is considered within the skill in the art to choose a pharmaceutically acceptable base.

Known benzodiazepine compounds have anxiolytic, anticonvulsant, sedative and/or skeletal muscle relaxant effect. The term "anticonvulsant" includes treatment of seizures, protection against seizure, reduction or amelioration of the intensity of seizure, reduction or amelioration of the frequency of seizure, and/or prevention of the occurrence or re-occurrence of seizure. In this regard, treatment of seizure includes cessation of an ongoing seizure, reduction in the severity of an ongoing seizure, reduction in the duration of an ongoing seizure. Protection against seizure includes forestalling an oncoming seizure.

Carrier System

Vitamin E is a class of fat soluble methylated phenols. There are at least eight naturally-occurring compounds that comprise this class: α-tocopherol, β-tocopherol, γ-tocopherol, δ-tocopherol, α-tocotrienol, β-tocotrienol, γ-tocotrienol, and δ-tocotrienol, all of which may be used in the compositions and methods of the present invention. There are multiple isomers of each of these compounds, all of which may be used in the compositions and methods of the present invention. There are also multiple esters of each of these compounds, including tocophersolan, all of which may be used in the compositions and methods of the present invention. As used herein, Vitamin E refers to any of the natural or synthetic tocopherols, tocotrienols, any isomers thereof, any esters thereof, any analogs or derivatives thereof, or any combinations thereof.

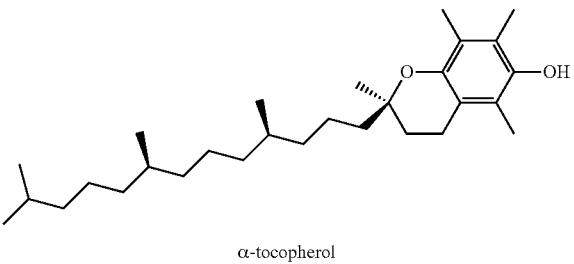 [SMILES: Cc1c(C)c2c(c(C)c1O)CC[C@@](C)(CCC[C@H](C)CCC[C@H](C)CCCC(C)C)O2]

α-tocopherol

The compounds that comprise Vitamin E are antioxidants. There is also evidence that they can prevent, delay the onset of, or ameliorate the symptoms of heart disease, cancer, cataracts, macular degeneration, glaucoma, Alzheimer's, and Parkinson's disease.

The inventors have found that Vitamin E can provide an effective carrier for benzodiazepine drugs. In some embodiments, benzodiazepines are soluble, or partially soluble, in Vitamin E. In some embodiments, Vitamin E may be present as microparticles, nanoparticles, or any combination thereof. Furthermore, use of Vitamin E can have the added benefit of either avoiding irritation of sensitive mucosal membranes and/or soothing irritated mucosal membranes.

Vitamin E is generally classified as hydrophobic, and when used as a carrier may be limited to formulations as an emulsion. However, emulsions can have several drawbacks. For instance, they may be difficult to create and can be highly unstable. Additionally, they can leave an oily film on the surface of the skin. Thus, to avoid the drawbacks of emulsions, some embodiments of the present invention comprise solutions of one or more benzodiazepine drugs in Vitamin E and one or more lower alkyl alcohols or one or more lower alkyl glycols, or any combinations thereof.

Lower alkyl alcohols are those with six or fewer carbon atoms. Thus, any of ethanol, propyl alcohol, butyl alcohol, pentanol, benzyl alcohol, any isomers thereof, or any combinations thereof can be used.

Lower alkyl glycols are those with six or fewer carbon atoms. Thus, any of ethylene glycol, propylene glycol, butylene glycol, pentylene glycol, any isomers thereof, or any combinations thereof can be used.

Additional Excipients

In some embodiments, a composition comprises at least one penetration enhancer in addition to a benzodiazepine drug, a natural or synthetic tocopherol or tocotrienol, and an alcohol or glycol. In some embodiments, the penetration enhancer is at least one alkyl glycoside. In some embodiments, the alkyl glycoside refers to any sugar joined to any hydrophobic alkyl, as described in U.S. Pat. No. 5,661,130, which is incorporated herein by reference in its entirety. The hydrophobic alkyl can be any suitable length, for example about 9 to about 24 carbons in length, especially about 10 to about 14 carbons in length. The hydrophobic alkyl can be branched and/or partially or wholly unsaturated. The alkyl may be joined to the saccharide core for example through a carbonyl group, whereby an ester group may be formed. A suitable alkyl glycoside will have the characteristics of being nontoxic, nonionic, and capable of increasing the absorption of a benzodiazepine drug when it is administered intranasally as described herein. Exemplary saccharides that may be covalently joined to an alkyl according to the present invention include glucose, maltose, maltotriose, maltotetrose, sucrose and trehalose. Exemplary alkyl glycosides that may be employed include octyl-, nonyl-, decyl-, undecyl-, dodecyl, tridecyl, tetradecyl, pentadecyl, octadecyl α- or β-D-maltoside, -glucoside or sucroside. In some embodiments, the preferred glycosides include maltose, sucrose or glucose linked by glycosidic linkage to an alkyl chain of 9, 10, 12, 14, 16, 18 or 20 carbon atoms. Specific excipients that may be employed in a nasal composition according to the invention include alkylsaccharide is dodecyl maltoside, tetradecyl maltoside, sucrose dodecanoate, sucrose monostearate, sucrose distearate, and/or combinations of two or more thereof. Alkyl glycosides that are particularly considered useful in embodiments of the invention include those marketed under the name Intravail® by Aegis Therapeutics, LLC, San Diego, Calif. Other alkyl glycosides may be selected from those having a hydrophile-lipophile balance (HLB) number of from about 10-20, especially about 11-15. The HLB number may be determined as set forth in the publication US2009/0047347, published on 19 Feb. 2009, the entirety of which, and especially paragraphs [0075]-[0079], is incorporated herein by reference. Where present, the amount of alkyl glycoside in the composition is sufficient to enhance the absorption of a benzodiazepine drug administered by the intranasal route. In some embodiments, the amount of alkyl glycoside in the composition is selected so as to enhance absorption of the benzodiazepine drug, while at the same time not significantly irritating the nasal mucosa. In some embodiments, the amount of alkyl glycoside in the composition is in a range of about 0.01% (w/v) to about 1% (w/v). In some embodiments, the amount of alkyl glycoside in the composition is in a range of about 0.05% (w/v) to about 0.5% (w/v), or about 0.125% (w/v) to about 0.5% (w/v).

The term "penetration enhancer", means any material which acts to increase absorption across the mucosa and/or increases bioavailability. In some embodiments, such materials include mucolytic agents, degradative enzyme inhibitors and compounds which increase permeability of the mucosal cell membranes. Whether a given compound is an "enhancer" can be determined by comparing two formulations comprising a non-associated, small polar molecule as the drug, with or without the enhancer, in an in vivo or good model test and determining whether the uptake of the drug is enhanced to a clinically significant degree. The enhancer should not produce any problems in terms of chronic toxicity because in vivo the enhancer should be non-irritant and/or rapidly metabolized to a normal cell constituent that does not have any significant irritant effect.

In some embodiments, preferred enhancing materials lysophospholipids, for example lysophosphatidylcholine obtainable from egg or soy lecithin. Other lysophosphatidylcholines that have different acyl groups as well as lyso compounds produced from phosphatidylethanolamines and phosphatidic acid which have similar membrane modifying properties may be used. Acyl carnitines (e.g. palmitoyl-dl-carnitine-chloride) is an alternative. In some embodiments, a suitable concentration is from 0.02 to 20% (w/v).

In some embodiments, enhancing agents that are appropriate include chelating agents (EGTA, EDTA, alginates), surface active agents (especially non-ionic materials), acyl glycerols, fatty acids and salts, tyloxapol and biological detergents listed in the SIGMA Catalog, 1988, page 316-321 (which is incorporated herein by reference). Also agents that modify the membrane fluidity and permeability are appropriate such as enamines (e.g. phenylalanine enamine of ethylacetoacetate), malonates (e.g. diethyleneoxymethylene malonate), salicylates, bile salts and analogues and fusidates. Suitable concentrations are up to 20% (w/v).

Thus, in some embodiments, the invention provides a pharmaceutical composition for nasal administration comprising: a benzodiazepine drug, one or more natural or synthetic tocopherols or tocotrienols, or any combinations thereof, in an amount from about 30% to about 95% (w/w); one or more alkyl glycosides; and one or more alcohols or glycols, or any combinations thereof, in an amount from about 10% to about 70% (w/w), in a pharmaceutically-acceptable formulation for administration to one or more nasal mucosal membranes of a patient. In some embodiments, the alkyl glycoside is an Intravail® brand alkyl glycoside. In some embodiments, the alkyl glycoside is dodecyl maltoside, tetradecyl maltoside, sucrose dodecanoate, sucrose monostearate, sucrose distearate, and/or a combination of two or more thereof. In some embodiments, the alkyl glycoside is dodecyl maltoside. In some embodiments, the alkyl glycoside is tetradecyl maltoside. In some embodiments, the alkyl glycoside is sucrose dodecanoate. In some embodiments, the alkyl glycoside is sucrose monostearate. In some embodiments, the alkyl glycoside is sucrose distearate. In some embodiments, the alkyl glycoside is a combination of two or more of dodecyl maltoside, tetradecyl maltoside, sucrose dodecanoate, sucrose monostearate, or sucrose distearate.

Thus, in some embodiments, the invention provides a pharmaceutical composition for nasal administration comprising: a benzodiazepine drug, which benzodiazepine drug comprises microparticles, nanoparticles or both, one or more natural or synthetic tocopherols or tocotrienols, or any combinations thereof, in an amount from about 30% to about 95% (w/w); one or more alkyl glycosides; and one or more alcohols or glycols, or any combinations thereof, in an amount from about 10% to about 70% (w/w), in a pharmaceutically-acceptable formulation for administration to one or more nasal mucosal membranes of a patient. In some embodiments, the alkyl glycoside is an Intravail® brand alkyl glycoside. In some embodiments, the alkyl glycoside is dodecyl maltoside, tetradecyl maltoside, sucrose dodecanoate, sucrose monostearate, sucrose distearate, and/or a combination of two or more thereof. In some embodiments, the alkyl glycoside is dodecyl maltoside. In some embodiments, the alkyl glycoside is tetradecyl maltoside. In some embodiments, the alkyl glycoside is sucrose dodecanoate. In some embodiments, the alkyl glycoside is sucrose monostearate. In some embodiments, the alkyl glycoside is sucrose distearate. In some embodiments, the alkyl glycoside is a combination of two or more of dodecyl maltoside, tetradecyl maltoside, sucrose dodecanoate, sucrose monostearate, or sucrose distearate.

Mucosal Membrane Preparations

Mucosal membrane preparations are generally administered in metered sprays having volumes of less than 250 µL, preferably less than 150 µL, and ideally from 25 to 100 µL. Although not prohibited in this invention, administration of volumes larger than about 300 µL per dose usually exceeds the absorption capacity of the membranes. This results in a large portion of the pharmaceutically-active ingredient being lost.

The dosage volume of preparations, in particular nasal preparations, preferably ranges from 25 to 100 µL. Volumes in excess of the aforementioned ranges may bypass the sinuses and flow down the back of the throat where the excess is swallowed.

Alprazolam

The dosage of alprazolam varies by indication, however it is expected that a therapeutic dose will be in the range of about 0.5 to about 4, preferably about 1 to about 2 mg per dose, from 1 to 8, preferably from 2 to 8, and in some preferred embodiments about 4 to about 6 times per day. Alprazolam may be manufactured using the process disclosed in U.S. Pat. No. 3,987,052, which is incorporated herein by reference in its entirety.

As a nasal formulation, alprazolam may be administered in 25 to 250 µL metered sprays. In some preferred embodiments, alprazolam is administered in 50 to 150 µL, especially about 100 µL, metered sprays Diazepam The dosage of diazepam may vary by indication, however it is expected that a therapeutic dose will be in the range of about 1 to about 20, preferably about 2 to about 10 mg per dose, from 1 to 8, preferably from 2 to 8, and in some preferred embodiments about 4 to about 6 times per day. Diazepam may be manufactured using the process disclosed in one of U.S. Pat. Nos. 3,371,085, 3,109,843, 3,136,815 or 3,102,116, each of which is incorporated herein by reference in its entirety.

As a nasal formulation, diazepam may be administered in 25 to 250 µL metered sprays. In some preferred embodiments, diazepam is administered in 50 to 150 µL, especially about 100 µL, metered sprays.

Flurazepam

The dosage of flurazepam varies by indication, however it is expected that a therapeutic dose will be in the range of about 5 to 40, preferably about 20 to about 35 mg per dose, from 1 to 8, preferably from 2 to 8, and in some preferred embodiments about 4 to about 6 times per day. Flurazepam may be manufactured using the process disclosed in U.S. Pat. Nos. 3,567,710 or 3,299,053, each of which is incorporated herein by reference in its entirety.

As a nasal formulation, flurazepam may be administered in 25 to 250 µL metered sprays. In some preferred embodiments, flurazepam is administered in 50 to 150 µL, especially about 100 µL, metered sprays.

Lorazepam

The dosage of Lorazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Lorazepam may be manufactured using the process disclosed in U.S. Pat. No. 3,296,249, which is incorporated herein by reference in its entirety.

As a nasal formulation, lorazepam may be administered in 25 to 250 µL metered sprays. In some preferred embodiments, lorazepam is administered in 50 to 150 µL, especially about 100 µL, metered sprays.

Medazepam

The dosage of medazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Medazepam may be manufactured using the process disclosed in U.S. Pat. No. 3,243,427, which is incorporated herein by reference in its entirety.

As a nasal formulation, medazepam may be administered in 25 to 250 µL metered sprays. In some preferred embodiments, medazepam is administered in 50 to 150 µL, especially about 100 µL, metered sprays.

Mexazolam

The dosage of mexazolam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Mexazolam may be manufactured using the process disclosed in U.S. Pat. No. 3,722,371, which is incorporated herein by reference in its entirety.

As a nasal formulation, mexazolam may be administered in 25 to 250 µL metered sprays. In some preferred embodiments, mexazolam is administered in 50 to 150 µL, especially about 100 µL, metered sprays.

Midazolam

The dosage of midazolam varies by indication, however it is expected that a therapeutic dose will be in the range of about 0.1 to about 20, preferably about 0.2 to about 10 mg per dose, from 1 to 8, preferably from 2 to 8, and in some preferred embodiments about 4 to about 6 times per day. Midazolam may be manufactured using the process disclosed in one of U.S. Pat. Nos. 4,280,957 or 5,831,089, each of which is incorporated herein by reference in its entirety.

As a nasal formulation, midazolam may be administered in 25 to 250 µL metered sprays. In some preferred embodiments, midazolam is administered in 50 to 150 µL, especially about 100 µL, metered sprays.

Temazepam

The dosage of temazepam varies by indication, however it is expected that a therapeutic dose will be in the range of about 1 to about 50, preferably about 5 to about 30 mg per dose, from 1 to 8, preferably from 2 to 8, and in some preferred embodiments about 4 to about 6 times per day.

Temazepam may be manufactured using the process disclosed in U.S. Pat. Nos. 3,340,253 or 3,374,225, each of which is incorporated herein by reference in its entirety.

As a nasal formulation, temazepam may be administered in 25 to 250 μL metered sprays. In some preferred embodiments, temazepam is administered in 50 to 150 μL, especially about 100 μL, metered sprays.

Formulation

Some embodiments comprise administering to one or more mucosal membranes of a patient a therapeutically effective amount of one or more benzodiazepine drugs, or pharmaceutically-acceptable salts thereof. Some embodiments of the composition disclose a composition comprising one or more benzodiazepine drugs or pharmaceutically-acceptable salts thereof in a concentration up to about 600 mg/mL. Other compositions disclose a composition comprising one or more benzodiazepine drugs or pharmaceutically-acceptable salts thereof in a concentration of about 10 mg/mL up to about 250 mg/mL. Further, some embodiments disclose a composition comprising one or more benzodiazepine drugs or pharmaceutically-acceptable salts thereof in a concentration of about 20 mg/mL up to about 50 mg/mL.

Some embodiments disclose a carrier system that is about 50% to about 90% (w/w) Vitamin E and about 10% to about 50% (w/w) lower alcohol or lower alkyl glycol, or any combinations thereof. Some embodiments disclose a carrier system that is about 65% to about 75% (w/w) Vitamin E and about 25% to about 35% (w/w) lower alkyl alcohol or lower alkyl glycol, or any combinations thereof. Further, some embodiments disclose a carrier system that is about 70% (w/w) Vitamin E and about 30% (w/w) lower alkyl alcohol or lower alkyl glycol, or any combinations thereof.

Some embodiments of the invention provide a method of administering the benzodiazepine drug composition to a patient. The preferred embodiment comprises use of diazepam. Some embodiments of the method disclose a dosage level of diazepam of about 1.0 mg to about 20.0 mg until achievement of the desired result. Other dosage levels disclose a dosage level of about 2.0 mg to about 15.0 mg until the desired result is achieved. Some embodiments disclose a dosage level of about 5.0 mg to about 10.0 mg until the desired result is achieved.

In some embodiments of the method, the dosage volume ranges from about 10 μL to about 200 μL. In some embodiments, the dosage volume ranges from about 20 μL to about 180 μL. Further, some embodiments disclose a dosage volume of about 50 μL to about 140 μL. In some embodiments, the dosage volume is 50 μL, 75 μL or 100 μL per nostril.

Formulation Process

In some embodiments, the composition for nasal administration is substantially free of benzodiazepine microparticles, nanoparticles or combinations thereof. In some embodiments, the composition is made by slowly warming or heating the Vitamin E until it is liquefied. Next, the one or more benzodiazepine drugs are added. The mixture is stirred and heated until the one or more benzodiazepine drugs dissolve or are substantially dissolved. Next, the one or more alcohols or glycols, or any combinations thereof, are added to the composition. This composition is stirred until a less viscous composition is achieved.

The formulation process may be adjusted to take into consideration variations in the formulation. For example, as depicted in FIG. 4, formulations comprising both benzyl alcohol and ethanol may be formulated by first combining Vitamin E, benzyl alcohol and ethanol (e.g., dehydrated alcohol, USP), mixing until the ingredients are homogenous, heating the mixture to about 45° C. (±2° C.), adding alkyl glocoside and mixing until the alkyl glycoside is dissolved and the solution is homogenous, adding benzodiazepine (e.g., diazepam) while maintaining the mixture at about 45° C., cooling the solution to about 25° C. (±2° C.) and adding ethanol (Q.S.) to achieve the final target weight of solution, mixing well to assure homogeneity. Solutions manufactured according to this process may be formulated in different concentrations of diazepam. For example, some embodiments of the invention include diazepam formulations summarized in the following table. While diazepam is used as an illustration in FIG. 4 and the following table, any benzodiazepines may also be used, such as alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, any pharmaceutically-acceptable salts thereof, and any combinations thereof.

NRL-1 Quantitative Composition. In some embodiments, the formulations are for nasal administration.

| | Solution Concentration | | |
|---|---|---|---|
| Component | 50 mg/mL | 75 mg/mL | 100 mg/mL |
| Vitamin E | 56.47 mg | 56.47 mg | 56.47 mg |
| Benzyl alcohol | 10.50 mg | 10.50 mg | 10.50 mg |
| Diazepam | 5.00 mg | 7.50 mg | 10.00 mg |
| Intravail A3 ® | 0.25 mg | 0.25 mg | 0.25 mg |
| Dehydrated ethanol | q.s. to 100 μL | q.s. to 100 μL | q.s. to 100 μL |

In some embodiments, the aforementioned formulations are sterile solutions with a bacteria count of 10 below the allowable level on a per mL basis. Additionally, pathogens are preferably absent. In some embodiments, the solutions are self-preserving, self-sterile or both.

In some embodiments, the benzodiazepine drug is formulated as a microparticulate and/or nanoparticulate suspension of the benzodiazepine. Preparation of microparticulate and nanoparticulate benzodiazepine may be accomplished by methods such as milling, etc. Such methods are known to those skilled in the art.

FIG. 5 depicts one embodiment of a process of manufacturing a suspension of benzodiazepine according to the instant invention. First, the benzodiazepine (e.g., diazepam) is sieved to produce a micronized benzodiazepine (e.g., diazepam). The micronized benzodiazepine (e.g., diazepam) is then split into two intermediates products—Diazepam A (high pressure) is a small particle size (mean particle size<2000 nm) and Diazepam B (low pressure) is a large particle size (mean particle diameter>2000 nm). After in-process testing, the two intermediate products are combined with one or more excipients in correct proportions to produce a bimodal particle suspension having a pre-selected mean particle diameter, which in some embodiments is greater than 2000 nm. In some embodiments, the excipients are prepared according to the second column in FIG. 5, e.g. by first combining propylene glycol, water and vitamin E polyethylene glycol succinate to form a mixture and heating the mixture until the ingredients are dissolved, then adding methylparaben, propyl paraben and Intravail™ (alkyl glycoside) to the mixture and mixing until the newly added ingredients are dissolved, and finally cooling the mixture, e.g. to 25° C.±2° C. The excipients can then be combined with Micronized Diazepam A and Micronized Diazepam B and mixed vigorously to disperse the micronized Diazepam to form the suspension. Next, povidone is added to the mixture, which is mixed until the povidone is fully dissolved. Finally, the suspension is brought to its final target weight with purified water and mixed well to achieve homogeneity. The final product can then be filled into suitable containers. In some embodiments, 3 mL may be filled into 4 mL amber glass vials with PTFE lined phenolic closures, though other containers are of course possible and contemplated within the scope of the invention. As diazepam is depicted in FIG. 5 as an exemplary benzodiazepine, any benzodiazepines, such as alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, any pharmaceutically-acceptable salts thereof, and any combinations thereof may also be employed.

In some embodiments, the aforementioned formulations are sterile suspensions with a bacteria count of 10 below the allowable level on a per mL basis. Additionally, pathogens are preferably absent. In some embodiments, the suspensions are self-preserving, self-sterile or both.

In some embodiments, the benzodiazepine drug is formulated as a solution. It is considered an aspect of the invention that employment of microparticulate and/or nanoparticulate benzodiazepine drug during the process of preparing the formulation, can improve the overall solubility of the benzodiazepine drug in the solvent system.

Additional Active and Inactive Ingredients

Additionally, some embodiments of the compositions and methods of using the compositions comprise an additional ingredient in the composition selected from active ingredients. By way of non-limiting example, such active ingredients include insulin, calcitonins (for example porcine, human, salmon, chicken, or eel) and synthetic modifications thereof, enkephalins, LHRH and analogues (Nafarelin, Buserelin, Zolidex), GHRH (growth hormone releasing hormone), nifedipin, THF (thymic humoral factor), CGRP (calcitonin gene related peptide), atrial natriuretic peptide, antibiotics, metoclopramide, ergotamine, Pizotizin, nasal vaccines (particularly HIV vaccines, measles, rhinovirus Type 13 and respiratory syncitial virus), pentamidine, CCK (Cholecystikinine), DDVAP, Interferons, growth hormone (solatotropir polypeptides or their derivatives (preferably with a molecular weight from 1000 to 300000), secretin, bradykinin antagonists, GRF (Growth releasing factor), THF, TRH (Thyrotropin releasing hormone), ACTH analogues, IGF (Insulin like growth factors), CGRP (Calcitorin gene related peptide) Atrial Natriuretic peptide, Vasopressin and analogues (DDAVP, Lypressin), Metoclopramide, Migraine treatment (Dihydroergotamine, Ergometrine, Ergotamine, Pizotizin), Nasal Vaccines (Particularly AIDS vaccines) FACTOR VIII, Colony Stimulating factors, G-CSF (granulocyte-colony stimulating factor), EPO (Erythropoitin) PTH (Parathyroid hormone) or pharmaceutically acceptable salts or combinations thereof.

Additionally, some embodiments of the compositions and methods of using the compositions comprise an additional ingredient in the composition selected from other anticonvulsants. By way of non-limiting example, such active ingredients include: paraldehyde; aromatic allylic alcohols (such as stiripentol); barbiturates (e.g. phenobarbitol, primidone, methylphenobarbital, metharbital and barbexaclone); bromides (such as potassium bromide); carbamates (such as felbamate); carboxamides (such as carbamazepine and oxcarbazepine); fatty acids (such as valproic acid, sodium valproate, and divalproex sodium, vigabatrin, progabide, tiagabine); fructose, topiramate, Gaba analogs (e.g. gabapentin and pregabalin); hydantoins (e.g. ethotoin, phenyloin, mephenyloin and fosphenyloin); oxazolidinediones (such as paramethadione, trimethadione, ethadione); propionates (e.g. beclamide), pyrimidinediones (e.g. primidone); pyrrolidines (e.g. brivaracetam, levetiracetam and seletracetam); succinimides (e.g. ethosuximide, phensuximide and mesuximide); sulfonamides (e.g. acetazolamide, sulthiame, methazolamide and zonisamide); triazines (such as lamotrigine); ureas (such as pheneturide, phenacemide); valproylamides (such as valpromide and valnoctamide); as well as other anticonvulsants or pharmaceutically acceptable salts or combinations thereof.

Additionally, some embodiments of the compositions and methods of using the compositions comprise an additional ingredient in the composition selected from other anticonvulsants. By way of non-limiting example, such active ingredients include: antibiotics and antimicrobial agents such as tetracyline hydrochloride, leucomycin, penicillin, penicillin derivatives, erythromycin, gentamicin, sulphathiazole and nitrofurazone; local anaesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitroglycerine and papaverine hydrochloride; antiseptics such as chlorhexidine hydrochloride, hexylresorcinol, dequaliniumchloride and ethacridine; enzymes such as lysozyme chloride, dextranase; bone metabolism controlling agents such as vitamin D, active vitamin D and vitamin C; sex hormones; hypotensives; sedatives; anti-tumor agents; steroidal anti-inflammatory agents such as hydrocortisone, prednisone, fluticasone, prednisolone, triamcinolone, triamcinolone acetonide, dexamethasone, betamethasone, beclomethasone, and beclomethasone dipropionate; non-steroidal anti-inflammatory agents such as acetaminophen, aspirin, aminopyrine, phenylbutazone, medanamic acid, ibuprofen, diclofenac sodium, indomethacine, colchicine, and probenocid; enzymatic anti-inflammatory agents such as chymotrypsin and bromelain seratiopeptidase; anti-histaminic agents such as diphenhydramine hydrochloride, chlorpheniramine maleate and clemastine; anti-allergic agents and antitussive-expectorant antasthmatic agents such as sodium chromoglycate, codeine phosphate, and isoproterenol hydrochloride or pharmaceutically acceptable salts or combinations thereof.

Additionally, some embodiments of the compositions and methods of using the compositions comprise an additional inactive ingredient in the composition. By way of non-limiting example, minor amounts of ingredients such as stabilizers, coloring agents, pH adjusters, buffering agents, preservatives such as agents which may prevent degradation, wetting agents, and flavoring agents may also be present. Examples of coloring agents include β-carotene, Red No. 2 and Blue No. 1. Examples of preservatives include stearic acid, ascorbyl stearate and ascorbic acid. Examples of corrigents include menthol and citrus perfume.

In some embodiments, the drug delivery system of the invention may advantageously comprise an absorption enhancer. The term "enhancer", means any material which acts to increase absorption across the mucosa and/or increases bioavailability. In some embodiments, such materials include mucolytic agents, degradative enzyme inhibitors and compounds which increase permeability of the mucosal cell membranes. Whether a given compound is an "enhancer" can be determined by comparing two formulations comprising a non-associated, small polar molecule as the drug, with or without the enhancer, in an in vivo or good model test and determining whether the uptake of the drug is enhanced to a clinically significant degree. The enhancer should not produce any problems in terms of chronic toxicity because in vivo the enhancer should be non-irritant and/or rapidly metabolized to a normal cell constituent that does not have any significant irritant effect.

In some embodiments, preferred enhancing materials lysophospholipids, for example lysophosphatidylcholine obtainable from egg or soy lecithin. Other lysophosphatidylcholines that have different acyl groups as well as lyso compounds produced from phosphatidylethanolamines and phosphatidic acid which have similar membrane modifying properties may be used. Acyl carnitines (e.g. palmitoyl-dl-carnitine-chloride) is an alternative. In some embodiments, a suitable concentration is from 0.02 to 20% (w/v).

In some embodiments, enhancing agents that are appropriate include chelating agents (EGTA, EDTA, alginates), surface active agents (especially non-ionic materials), acyl glycerols, fatty acids and salts, tyloxapol and biological detergents listed in the SIGMA Catalog, 1988, page 316-321 (which is incorporated herein by reference). Also agents that modify the membrane fluidity and permeability are appropriate such as enamines (e.g. phenylalanine enamine of ethylacetoacetate), malonates (e.g. diethyleneoxymethylene malonate), salicylates, bile salts and analogues and fusidates. Suitable concentrations are up to 20% (w/v).

In some embodiments, the invention takes advantage of delivery of a drug incorporated into or onto a bioadhesive microsphere with an added pharmaceutical adjuvant applies to systems that contain active drug and mucolytic agent, peptidase inhibitors or non-drug polypeptide substrate singly or in combination. Suitably mucolytic agents are thiol-containing compounds such as N-acetylcysteine and derivatives thereof. Peptide inhibitors include actinonin, amastatin, bestatin, chloroacetyl-HOLeu-Ala-Gly-NH.sub.2, diprotin A and B, ebelactone A and B, E-64, leupeptin, pepstatin A, phisphoramidon, H-Thr-(tBu)-Phe-Pro-OH, aprotinin, kallikrein, chymostatin, benzamidine, chymotrypsin and trypsin.

Suitable concentrations are from 0.01 to 10% (w/v). The person skilled in the art will readily be able to determine whether an enhancer should be included.

Administration

In some embodiments, the administration of the composition comprises administering at least a portion of the therapeutically effective amount of the composition onto at least one mucosal membrane. In some embodiments, the administration of the composition comprises spraying at least a portion of the therapeutically effective amount of the composition into at least one nostril. In some embodiments, the administration of the composition comprises spraying at least a portion of the therapeutically effective amount of the composition into each nostril. In some embodiments, the administration of the composition comprises spraying a first quantity of the composition into the first nostril, spraying a second quantity of the composition into a second nostril, and optionally after a pre-selected time delay, spraying a third quantity of the composition into the first nostril. Some embodiments further comprise, optionally after a pre-selected time delay, administering at least a fourth quantity of the composition to the second nostril.

Alprazolam

The dosage of alprazolam varies by indication, however it is expected that a therapeutic dose will be in the range of about 0.5 to about 4, preferably about 1 to about 2 mg per dose, from 1 to 8, preferably from 2 to 8, and in some preferred embodiments about 4 to about 6 times per day. Alprazolam may be manufactured using the process disclosed in U.S. Pat. No. 3,987,052, which is incorporated herein by reference in its entirety.

As a nasal formulation, alprazolam may be administered in 25 to 250 µL metered sprays. In some preferred embodiments, alprazolam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Diazepam

The dosage of diazepam may vary by indication, however it is expected that a therapeutic dose will be in the range of about 1 to about 20, preferably about 2 to about 10 mg per dose, from 1 to 8, preferably from 2 to 8, and in some preferred embodiments about 4 to about 6 times per day. Diazepam may be manufactured using the process disclosed in one of U.S. Pat. Nos. 3,371,085, 3,109,843, 3,136,815 or 3,102,116, each of which is incorporated herein by reference in its entirety.

As a nasal formulation, diazepam may be administered in 25 to 250 µL metered sprays. In some preferred embodiments, diazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Flurazepam

The dosage of flurazepam varies by indication, however it is expected that a therapeutic dose will be in the range of about 5 to 40, preferably about 20 to about 35 mg per dose, from 1 to 8, preferably from 2 to 8, and in some preferred embodiments about 4 to about 6 times per day. Flurazepam may be manufactured using the process disclosed in U.S. Pat. Nos. 3,567,710 or 3,299,053, each of which is incorporated herein by reference in its entirety.

As a nasal formulation, flurazepam may be administered in 25 to 250 µL metered sprays. In some preferred embodiments, flurazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Lorazepam

The dosage of Lorazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Lorazepam may be manufactured using the process disclosed in U.S. Pat. No. 3,296,249, which is incorporated herein by reference in its entirety.

As a nasal formulation, lorazepam may be administered in 25 to 250 µL metered sprays. In some preferred embodiments, lorazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Medazepam

The dosage of medazepam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Medazepam may be manufactured using the process disclosed in U.S. Pat. No. 3,243,427, which is incorporated herein by reference in its entirety.

As a nasal formulation, medazepam may be administered in 25 to 250 µL metered sprays. In some preferred embodiments, medazepam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Mexazolam

The dosage of mexazolam varies by indication, however it is expected that a therapeutic dose will be in the range of about 0.1 to about 10, preferably about 0.2 to about 1 mg per dose, from 1 to 8, preferably from 2 to 8, and in some preferred embodiments about 4 to about 6 times per day. Mexazolam may be manufactured using the process disclosed in U.S. Pat. No. 3,722,371, which is incorporated herein by reference in its entirety.

As a nasal formulation, mexazolam may be administered in 25 to 250 µL metered sprays. In some preferred embodiments, mexazolam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Midazolam

The dosage of midazolam varies by indication, however it is expected that a therapeutic dose will be in the range of about 0.1 to about 20, preferably about 0.2 to about 10 mg per dose, from 1 to 8, preferably from 2 to 8, and in some preferred embodiments about 4 to about 6 times per day. Midazolam may be manufactured using the process disclosed in one of U.S. Pat. Nos. 4,280,957 or 5,831,089, each of which is incorporated herein by reference in its entirety.

As a nasal formulation, midazolam may be administered in 25 to 250 µL metered sprays. In some preferred embodiments, midazolam is administered in 50 to 150 µL, especially about 100 µL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Temazepam

The dosage of temazepam varies by indication, however it is expected that a therapeutic dose will be in the range of about 1 to about 50, preferably about 5 to about 30 mg per dose, from 1 to 8, preferably from 2 to 8, and in some preferred embodiments about 4 to about 6 times per day. Temazepam may be manufactured using the process disclosed in U.S. Pat. Nos. 3,340,253 or 3,374,225, each of which is incorporated herein by reference in its entirety.

As a nasal formulation, temazepam may be administered in 25 to 250 μL metered sprays. In some preferred embodiments, temazepam is administered in 50 to 150 μL, especially about 100 μL, metered sprays. In some embodiments, a first metered spray is applied to a first nostril and if necessary a second metered spray is applied to a second nostril. In some optional embodiments, a third metered spray is applied to the first nostril. In some embodiments, a fourth metered spray is applied to the second nostril. In some embodiments, additional metered sprays are applied to alternating nostrils until the full target therapeutic dose has been administered to the patient. In some embodiments, there is a time increment of from several seconds to 5 minutes, preferably about 10 seconds to about 1 minute, between applications of benzodiazepine drug to the same nostril. This allows time for the drug to cross the nasal mucosa and enter the blood stream. Multiple applications of metered sprays to each nostril, optionally separated by a time interval, allows administration of a full therapeutic dose in increments small enough to permit full absorption of the benzodiazepine drug into the blood stream and avoid loss of drug down the back of the throat.

Those skilled in the art will be aware that a systematic, therapeutically effective amount of benzodiazepine drugs for treating the aforementioned disorders will vary with age, size, weight, and general physical condition of the patient as well as the severity of the disease. Frequency of administration will likewise vary with the formulation of the composition and it can be adjusted so that any suitable number of doses per day may be used.

EXAMPLES

The invention will now be illustrated with reference to the following illustrative, non-limiting examples.

Example 1

A pharmaceutical composition comprising diazepam is prepared. It is formulated as a solution to be delivered via a nasal delivery device. The composition is used to treat or prevent seizures associated with epilepsy in adults. Treatment is administered either before or after a seizure has begun. If the patient is seizing, it is administered as 1 puff from any nasal delivery device (1 puff at 5.0 mg/puff (5.0 mg/0.1 mL and 0.1 mL/puff)) every 5 minutes until cessation of the seizure. However, it can be given as 1 puff per nostril in each nostril (2 puffs at 2.5 mg/puff (5.0 mg/0.1 mL and 0.05 mL/puff)) every 5 minutes until cessation of the seizure. The composition according to this example is set forth in the following table.

TABLE 1-1

| 5.0 mg/0.1 mL | Diazepam |
| 70.0 mg | α-tocopherol |
| 0.1 mL | ethanol (qs ad to 0.1 mL) |

Example 2

A pharmaceutical composition comprising diazepam is prepared. It is formulated as a solution to be delivered via a nasal delivery device. The composition is used to treat or prevent seizures associated with epilepsy in children. Treatment is administered either before or after a seizure has begun. If the patient is seizing, it is administered as 1 puff from any nasal delivery device (1 puff at 2.0 mg/puff (2.0 mg/0.1 mL and 0.1 mL/puff)). If the seizure fails to stop another dose may be administered after 5 minutes. However, it can be given as 1 puff per nostril in each nostril (2 puffs at 1.0 mg/puff (2.0 mg/0.1 mL and 0.05 mL/puff)). If the seizure fails to stop another dose may be administered after 5 minutes. The composition according to this example is set forth in the following table.

TABLE 2-1

| 2.0 mg/0.1 mL | Diazepam |
| 70.0 mg | α-tocopherol |
| 0.1 mL | ethanol (qs ad to 0.1 mL) |

Example 3

Formulation of Diazepam Solutions

In general, benzodiazepine solutions may be formulated by combining one or more natural or synthetic tocopherols or tocotrienols and one or more lower alcohols or glycols and mixing until a homogeneous mixture is formed, adding the benzodiazepine drug to the homogeneous mixture, heating and mixing the ingredients until the benzodiazepine is fully dissolved in the homogeneous mixture, cooling the mixture, and bringing the mixture to its final mass or volume with lower alcohol or glycol.

Two different diazepam solutions were formulated by the foregoing process. Vitamin E USP and dehydrated ethanol USP were combined in the amounts set forth in the following table and mixed to form a homogeneous mixture. Diazepam in the amounts set forth in the following table was then added to the homogeneous mixture. The ingredients were heated to 40-45° C. with mixing until the diazepam was fully dissolved, thereby forming a solution. The solution was cooled to 20-25° C., whereupon the solution was brought to its final target weight with dehydrated ethanol USP and the solution was mixed thoroughly to assure homogeneity. The solution was then sampled for in-process testing and packaged in 3 mL amber glass vials.

TABLE 3-1

Diazepam Solutions - 70 mg/mL

| Component | Solution 00 (65% Vitamin E) Concentration (mg/mL) | Solution 02 (80% Vitamin E) Concentration (mg/mL) |
| --- | --- | --- |
| Diazepam USP | 70.0 | 70.0 |
| Vitamin E USP | 650.0 | 800.0 |
| Dehydrated Ethanol USP | q.s. to 1 mL | q.s. to 1 mL |

Additional solutions of diazepam at varying concentrations are made in a similar manner, by varying the amount of diazepam and the relative amounts of Vitamin E and ethanol. Other benzodiazepine solutions are made by substituting one or more benzodiazepines for diazepam. Other ingredients, such as alkyl glycoside, can be added at a suitable step in the process (e.g. before or concurrently with the addition of benzodiazepine).

Example 4

Formulation of Diazepam Suspensions

In general, benzodiazepine suspensions are formulated by micronizing benzodiazepine and combining the benzodiazepine with a carrier. The carrier is prepared by combining one or more lower alcohols or glycols with water, adding a natural or synthetic tocopherol or tocotrienol, heating the mixture until the tocopherol or tocotrienol is dissolved, adding one or more parabens and mixing until the parabens are dissolved and cooling the carrier. Once the benzodiazepine is added to the carrier, additional excipients, such as surfactants, can optionally be added and dissolved in the carrier. The suspension is then brought up to its final mass or volume with water.

Two different diazepam suspensions were formulated by the foregoing general process. Two different diazepam particle sizes were prepared—A: a small particle size by prepared by high pressure micronization, and B: a large particle size prepared by low pressure micronization. The carrier was prepared by combining propylene glycol USP and purified water USP, then adding Vitamin E Polyethylene Glycols Succinate NF, then mixing and heating the combined ingredients to about 45° C. Mixing was continued until the Vitamin E Polyethylene Glycol Succinate was fully dissolved. The carrier was then cooled to 20-25° C. The micronized diazepam (A and B) was then added to the carrier with vigorous mixing until the diazepam was fully dispersed in the carrier. Polyvinylpyrrolidone Povidone USP/NF was then added to the mixture and mixed until fully dissolved. The suspension was then brought up to weight with purified water USP. The suspension was then mixed until homogeneous, sampled for in-process testing, and packaged in 3 mL amber glass bottles.

TABLE 4-1

Diazepam Suspension Formulations

| Component | Suspension 03 (200 mg/mL Diazepam) Concentration (mg/mL) | Suspension 01 (100 mg/mL Diazepam) Concentration (mg/mL) |
|---|---|---|
| Diazepam USP | 200.00 | 100.00 |
| Vitamin E Polyethylene Glycol Succinate NF | 100.0 | 100.0 |
| Methylparaben NF | 2.0 | 2.0 |
| Propylparaben NF | 0.5 | 0.5 |
| Propylene Glycol USP | 100.0 | 100.0 |
| Povidone USP/NF | 25.0 | 25.0 |
| Purified Water USP/EP | q.s. to 1 mL | q.s. to 1 mL |

Additional suspensions of diazepam at varying concentrations are made in a similar manner, by varying the amount of diazepam and optionally other excipients. Other benzodiazepine suspensions are made by substituting one or more benzodiazepines for diazepam. Other ingredients, such as alkyl glycoside, can be added at a suitable step in the process. For example, an alkylglycoside may be added to the carrier during compounding of the carrier, or may be added to the suspension mixture concurrently with or after addition of the povidone.

Example 5

Stability of Diazepam Solutions and Suspensions

Solutions 00 and 02 (Example 3) and Suspensions 01 and 03 (Example 4) were set up on stability at 25° C./60% RH, 30° C./65% RH and 40° C./75% RH. One batch each of four different formulations, packaged in 3-ml vials with screw-top closures, along with corresponding actuators, were set up at three storage conditions. They are listed in Table 1 with their corresponding Particle Sciences initial sample control numbers.

TABLE 5-1

Summary of PSI sample control numbers

| Formulation # | 25° C./60% RH | 30° C./65% RH | 40° C./75% RH |
|---|---|---|---|
| Solution 00 - 70 mg/ml solution, 65% Vitamin E | 083101.01 | 083101.02 | 083101.02 |
| Solution 02 - 70 mg/ml solution, 80% vitamin E | 083102.01 | 083102.02 | 083102.03 |
| Suspension 01 - 100 mg/mi suspension | 083103.01 | 083103.02 | 083103.03 |
| Suspension 03 - 200 mg/ml suspension | 083104.01 | 083104.02 | 083104.03 |

Samples were tested for spray content uniformity, spray volume, diazepam content, diazepam related substances, and methylparaben and propylparaben assay (suspension samples only). Unit weights were determined as per USP <755>.

Summaries of the average assay values and all other results are given in Tables 5-4, 5-5, 5-6 and 5-7. The results for the initial, 1-month and 3-month time points are also shown for comparison. Individual spray content uniformity results are given in Tables 5-8, 5-9, 5-10, 5-11, 5-12, 5-13, 5-14, and 5-15.

In general, all of the assays and the other results are similar to the initial data, with the exceptions of diazepam related compounds A and B.

Related compound A did not meet the specification of not more than (NMT) 0.01% for some samples (see Table 2). Related compound A has increased with time and temperature.

TABLE 5-2

Summary of related compound A T6M results

| Solution/Suspension # | 25° C./60% RH | 30° C./65% RH | 40° C./75% RH |
|---|---|---|---|
| Solution 00 | Meets specification | 0.058% | 0.051% |
| Solution 02 | Meets specification | Meets specification | Meets specification |
| Suspension 01 | 0.038% | 0.046% | 0.157% |
| Suspension 03 | 0.019% | 0.029% | 0.081% |

Related compound B is also increasing with time and temperature, and now fails specification of NMT 0.1% at 40° C. condition for both suspension and one solution formulation. Only formulation 2602 meets all impurity specifications.

TABLE 5-3

Summary of related compound B T6M results

| Solution/Suspension # | 25° C./60% RH | 30° C./65% RH | 40° C./75% RH |
|---|---|---|---|
| Solution 00 | Meets specification | Meets specification | 0.398% |
| Solution 02 | Meets specification | Meets specification | Meets specification |
| Suspension 01 | Meets specification | Meets specification | 0.289% |
| Suspension 03 | Meets specification | Meets specification | 0.123% |

TABLE 5-4

Summary of Solution 00 results

| Solution 00, 70 mg/ml, 65% Vitamin E | Specifications | Initial | 1 month 25° C./ 60% RH | 1 month 30° C./ 65% RH | 1 month 40° C./ 75% RH | 3 month 25° C./ 60% RH | 3 month 30° C./ 65% RH | 3 month 40° C./ 75% RH | 6 month 25° C./ 60% RH | 6 month 30° C./ 65% RH | 6 month 40° C./ 75% RH |
|---|---|---|---|---|---|---|---|---|---|---|---|
| Description | Yellow to orange solution | Amber solution | Amber solution | Amber solution | Amber solution | Amber solution | Amber solution | Amber solution | Amber solution | Amber solution | Amber solution |
| Identification - UV | Conforms to reference std. UV and RT | pass | N/A | N/A | N/A | N/A | N/A | N/A | N/A | N/A | N/A |
| Assay Diazepam (%) | 90.0 to 110.0% | 100.1 | 100.3 | 93.9 | 98.8 | 96.3 | 96.9 | 101.2 | 97.5 | 94.6 | 100.6 |
| Impurities (%) [1] | | | | | | | | | | | |
| Nordazepam | NMT 0.3% | 0.005 | 0.01 | 0.014 | 0.019 | 0.013 | 0.013 | 0.013 | 0.013 | 0.013 | 0.013 |
| Related Compound B | NMT 0.1% | ND | 0.002 | 0.007 | 0.03 | 0.008 | 0.016 | 0.089 | 0.024 | 0.098 | 0.398 |
| Related Compound A | NMT 0.01% | 0.002 | 0.002 | 0.004 | 0.011 | 0.002 | 0.002 | 0.01 | 0.005 | 0.058 | 0.051 |
| Unknown | NMT 0.1% | 0.011 | 0.012 | 0.014 | 0.02 | 0.037 | 0.039 | 0.047 | 0.035 | 0.066 | 0.055 |
| Total | NMT 1.0% | 0.0 | 0.0 | 0.0 | 0.1 | 0.1 | 0.1 | 0.2 | 0.1 | 0.2 | 0.5 |
| Microbial Limits | Meets USP {61} | pass | N/A | N/A | N/A | N/A | N/A | N/A | pass | not tested | not tested |
| Fill weight (g) | report results | 1.108 | 1.105 | 1.111 | 1.112 | 1.109 | 1.109 | 1.113 | 1.103 | 1.111 | 1.109 |
| Fill volume (ml) | report results | 1.192 | 1.189 | 1.195 | 1.196 | 1.193 | 1.193 | 1.198 | 1.187 | 1.195 | 1.193 |
| Spray delivered (µl) | report results | 133.9 | 140.7 | 146.8 | 140.5 | 149.1 | 143.5 | 139.6 | 131.4 | not tested | 136.4 |
| Average Spray Content (%) | report results | 95.0 | 101.2 | 100.4 | 99.4 | 99.7 | 94.6 | 99.4 | 95.7 | not tested | 108.7 |
| Viscosity (Pa*s) | report results | 0.14 | 0.086 | 0.12 | 0.12 | 0.096 | 0.14 | 0.12 | 0.12 | 0.11 | 0.11 |

[1] LOQ is approximately 0.006%, LOD is approximately 0.002%. Results below LOQ are reported in this table for trending purposes.

TABLE 5-5

Summary of Solution 02 results

| Solution 02, 70 mg/ml, 65% Vitamin E | Specifications | Initial | 1 month 25° C./ 60% RH | 1 month 30° C./ 65% RH | 1 month 40° C./ 75% RH | 3 month 25° C./ 60% RH | 3 month 30° C./ 65% RH | 3 month 40° C./ 75% RH | 6 month 25° C./ 60% RH | 6 month 30° C./ 65% RH | 6 month 40° C./ 75% RH |
|---|---|---|---|---|---|---|---|---|---|---|---|
| Description | Yellow to orange sol'n | Amber sol'n | Amber sol'n | Amber sol'n | Amber sol'n | Amber sol'n | Amber sol'n | Amber sol'n | Amber sol'n | Amber sol'n | Amber sol'n |
| Identification - UV | Conforms to reference std. UV and RT | pass | N/A | N/A | N/A | N/A | N/A | N/A | N/A | N/A | N/A |
| Assay Diazepam (%) | 90.0 to 110.0% | 100.5 | 94.9 | 96.2 | 103.3 | 98.0 | 97.2 | 99.6 | 97.0 | 94.3 | 100.3 |
| Impurities (%) [1] | | | | | | | | | | | |
| Nordazepam | NMT 0.3% | 0.003 | 0.004 | 0.005 | 0.006 | 0.005 | 0.005 | 0.006 | 0.005 | 0.004 | 0.005 |
| Related Compound B | NMT 0.1% | ND | 0.002 | 0.003 | 0.006 | 0.003 | 0.005 | 0.032 | 0.007 | 0.020 | 0.058 |
| Related Compound A | NMT 0.01% | 0.003 | 0.002 | 0.002 | 0.003 | 0.002 | 0.002 | 0.004 | 0.003 | 0.009 | 0.007 |
| Unknown | NMT 0.1% | 0.01 | 0.012 | 0.014 | 0.018 | 0.019 | 0.025 | 0.032 | 0.014 | 0.020 | 0.018 |
| Total | NMT 1.0% | 0.0 | 0.0 | 0.0 | 0.0 | 0.0 | 0.0 | 0.1 | 0.0 | 0.1 | 0.1 |
| Microbial Limits | Meets USP {61} | pass | N/A | N/A | N/A | N/A | N/A | N/A | pass | not tested | not tested |
| Fill weight (g) | report results | 1.135 | 1.117 | 1.128 | 1.123 | 1.116 | 1.133 | 1.137 | 1.124 | 1.133 | 1.127 |
| Fill volume (ml) | report results | 1.184 | 1.165 | 1.177 | 1.172 | 1.164 | 1.182 | 1.186 | 1.172 | 1.183 | 1.176 |
| Spray delivered (µl) | report results | 115.0 | 137.5 | 137.6 | 133.1 | 143.9 | 136.3 | 143.8 | 129.3 | not tested | 124.2 |

TABLE 5-5-continued

Summary of Solution 02 results

| Solution 02, 70 mg/ml, 65% Vitamin E | Specifications | Initial | 1 month 25° C./ 60% RH | 1 month 30° C./ 65% RH | 1 month 40° C./ 75% RH | 3 month 25° C./ 60% RH | 3 month 30° C./ 65% RH | 3 month 40° C./ 75% RH | 6 month 25° C./ 60% RH | 6 month 30° C./ 65% RH | 6 month 40° C./ 75% RH |
|---|---|---|---|---|---|---|---|---|---|---|---|
| Average Spray Content (%) | report results | 98.6 | 97.6 | 97.7 | 100.7 | 98.7 | 94.7 | 100.5 | 95.8 | not tested | 97.1 |
| Viscosity (Pa*s) | report results | 0.69 | 0.68 | 0.64 | 0.68 | 0.63 | 0.65 | 0.64 | 0.61 | 0.55 | 0.56 |

[1] LOQ is approximately 0.006%, LOD is approximately 0.002%. Results below LOQ are reported in this table for trending purposes.

TABLE 5-6

Summary of Suspension 01 results

| Suspension 01, 100 mg/ml | Specifications | Initial | 1 month 25° C./ 60% RH | 1 month 30° C./ 65% RH | 1 month 40° C./ 75% RH | 3 month 25° C./ 60% RH | 3 month 30° C./ 65% RH | 3 month 40° C./ 75% RH | 6 month 25° C./ 60% RH | 6 month 30° C./ 65% RH | 6 month 40° C./ 75% RH |
|---|---|---|---|---|---|---|---|---|---|---|---|
| Description | Cloudy to white solution | White dispersion | White dispersion | White dispersion | White dispersion | White dispersion | White dispersion | White dispersion | White dispersion | pale yellow dispersion | yellow dispersion |
| Identification - UV | Conforms to reference std. UV and RT | Pass | N/A | N/A | N/A | N/A | N/A | N/A | N/A | N/A | N/A |
| Assay Diazepam (%) | 90.0 to 110.0% | 102.8 | 102.6 | 100.9 | 104.3 | 101.3 | 101.8 | 103.6 | 100.7 | 104.3 | 99.4 |
| Impurities (%) [1] | | | | | | | | | | | |
| Nordazepam | NMT 0.3% | ND | ND | ND | ND | ND | ND | ND | ND | ND | ND |
| Related Compound B | NMT 0.1% | ND | ND | ND | 0.004 | ND | 0.004 | 0.053 | 0.005 | 0.013 | 0.289 |
| Related Compound A | NMT 0.01% | ND | 0.01 | 0.02 | 0.034 | 0.026 | 0.036 | 0.08 | 0.038 | 0.046 | 0.157 |
| Unknown | NMT 0.1% | 0.008 | 0.008 | 0.008 | 0.008 | 0.008 | 0.007 | 0.007 | 0.008 | 0.007 | 0.018 |
| Total | NMT 1.0% | 0.0 | 0.0 | 0.0 | 0.0 | 0.0 | 0.0 | 0.1 | 0.1 | 0.1 | 0.5 |
| Methylparaben (%) | 80.0%-115.% | 97.7 | 100.2 | 92.1 | 100.3 | 101.4 | 100.6 | 101.6 | 106.0 | 103.2 | 103.2 |
| Propylparaben (%) | 80.0%-115.0% | 100.2 | 100.5 | 92.2 | 99.2 | 100.6 | 99 | 100 | 98.5 | 97.6 | 96.7 |
| Microbial Limits | Meets USP {61} | Pass | N/A | N/A | N/A | N/A | N/A | N/A | pass | not tested | not tested |
| Fill weight (g) | report results | 1.254 | 1.252 | 1.252 | 1.244 | 1.246 | 1.248 | 1.247 | 1.245 | 1.242 | 1.235 |
| Fill volume (ml) | report results | 1.198 | 1.196 | 1.196 | 1.188 | 1.191 | 1.193 | 1.191 | 1.190 | 1.187 | 1.180 |
| Spray delivered (μl) | report results | 132.5 | 131.2 | 126 | 123.9 | 137.6 | 137.8 | 136.3 | 140.0 | not tested | 137.6 |
| Average Spray Content (%) | report results | 92.2 | 94.2 | 91.1 | 89.9 | 101.5 | 100.4 | 95.3 | 101.8 | not tested | 95.94 |
| Viscosity (Pa*s) | report results | 0.0098 | 0.0098 | 0.0092 | 0.0090 | 0.0092 | 0.0093 | 0.0089 | 0.0082 | 0.0080 | 0.0092 |

[1] LOQ is approximately 0006%, LOD is approximatelyo.002%. Results below LOQ are reported in this table for trending purposes.

TABLE 5-7

Summary of Suspension 03 results

| Suspension 03, 200 mg/mL | Specifications | Initial | 1 month 25° C./ 60% RH | 1 month 30° C./ 65% RH | 1 month 40° C./ 75% RH | 3 month 25° C./ 60% RH | 3 month 30° C./ 65% RH | 3 month 40° C./ 75% RH | 6 month 25° C./ 60% RH | 6 month 30° C./ 65% RH | 6 month 40° C./ 75% RH |
|---|---|---|---|---|---|---|---|---|---|---|---|
| Description | Cloudy to white dispersion | White dispersion | White dispersion | White dispersion | White dispersion | White dispersion | White dispersion | White dispersion | White dispersion | pale yellow dispersion | yellow dispersion |
| Identification - UV | Conforms to reference std. UV and RT | Pass | N/A | N/A | N/A | N/A | N/A | N/A | N/A | N/A | N/A |

TABLE 5-7-continued

Summary of Suspension 03 results

| Suspension 03, 200 mg/mL | Specifications | Initial | 1 month 25° C./ 60% RH | 1 month 30° C./ 65% RH | 1 month 40° C./ 75% RH | 3 month 25° C./ 60% RH | 3 month 30° C./ 65% RH | 3 month 40° C./ 75% RH | 6 month 25° C./ 60% RH | 6 month 30° C./ 65% RH | 6 month 40° C./ 75% RH |
|---|---|---|---|---|---|---|---|---|---|---|---|
| Assay Diazepam (%) | 90.0 to 110.0% | 100.7 | 101.2 | 98.9 | 101.6 | 102.6 | 103.6 | 103.1 | 100.5 | 98.9 | 100.1 |
| Impurities (%) [1] | | | | | | | | | | | |
| Nordazepam | NMT 0.3% | ND | ND | ND | ND | ND | ND | ND | ND | ND | ND |
| Related Compound B | NMT 0.1% | ND | ND | ND | ND | 0.002 | ND | 0.023 | 0.002 | 0.008 | 0.123 |
| Related Compound A | NMT 0.01% | ND | 0.005 | 0.01 | 0.017 | 0.017 | 0.012 | 0.039 | 0.019 | 0.029 | 0.081 |
| Unknown | NMT 0.1% | 0.008 | 0.008 | 0.008 | 0.008 | 0.008 | 0.008 | 0.008 | 0.008 | 0.007 | 0.008 |
| Total | NMT 1.0% | 0.0 | 0.0 | 0.0 | 0.0 | 0.0 | 0.0 | 0.1 | 0.0 | 0.0 | 0.2 |
| Methylparaben (%) | 80.0%-115.% | 93.4 | 101.1 | 93.8 | 99.7 | 101.5 | 101.6 | 101.2 | 103.5 | 97.2 | 102.1 |
| Propylparaben (%) | 80.0%-115.0% | 95.6 | 100.2 | 94 | 98.4 | 100.1 | 101.3 | 99.2 | 97.1 | 91.9 | 95.9 |
| Microbial Limits | Meets USP {61} | Pass | N/A | N/A | N/A | N/A | N/A | N/A | pass | not tested | not tested |
| Fill weight (g) | report results | 1.276 | 1.28 | 1.259 | 1.272 | 1.279 | 1.279 | 1.276 | 1.280 | 1.262 | 1.260 |
| Fill volume (ml) | report results | 1.186 | 1.19 | 1.171 | 1.183 | 1.19 | 1.19 | 1.187 | 1.190 | 1.173 | 1.172 |
| Spray delivered (μl) | report results | 112.4 | 137.4 | 134.3 | 119.9 | 138.9 | 139.3 | 134.3 | 149.4 | not tested | 138.0 |
| Average Spray Content (%) | report results | 82.8 | 99.3 | 97.3 | 86.7 | 98.6 | 102.3 | 96.2 | 98.2 | not tested | 98.7 |
| Viscosity (Pa*s) | report results | 0.021 | 0.017 | 0.017 | 0.019 | 0.016 | 0.016 | 0.018 | 0.014 | 0.013 | 0.015 |

[1] LOQ is approximately 0.006%, LOD is approximately 0.002%. Results below LOQ are reported in this table for trending purposes.

TABLE 5-8

Solution 00 25° C./60% RH spray content uniformity results

| Sample | Weight Collected, g | Weight Actuated, g | Diazepam Recovered, mg | % Diazepam Recovered |
|---|---|---|---|---|
| 1 | 0.13061 | 0.13259 | 9.59355 | 97.89 |
| 2 | 0.13217 | 0.13451 | 9.78206 | 99.82 |
| 3 | 0.12365 | 0.13332 | 8.85797 | 90.39 |
| 4 | 0.12761 | 0.13072 | 9.39720 | 95.89 |
| 5 | 0.14702 | 0.15216 | 8.91438 | 90.96 |
| 6 | 0.13414 | 0.13702 | 9.22442 | 94.13 |
| 7 | 0.12959 | 0.13384 | 9.84590 | 100.47 |
| 8 | 0.12367 | 0.14603 | 8.88093 | 90.62 |
| 9 | 0.13367 | 0.13425 | 9.92610 | 101.29 |
| Average | 0.13135 | 0.13716 | 9.380 | 95.72 |
| St. Dev. | 0.0070 | 0.0071 | 0.4309 | 4.3970 |
| % RSD | 5.35 | 5.20 | 4.59 | 4.59 |

TABLE 5-9

Solution 00 40° C./75% RH spray content uniformity results

| Sample | Weight Collected, g | Weight Actuated, g | Diazepam Recovered, mg | % Diazepam Recovered |
|---|---|---|---|---|
| 1 | 0.14139 | 0.15111 | 10.57237 | 107.88 |
| 2 | 0.14731 | 0.15146 | 11.62831 | 118.66 |
| 3 | 0.14489 | 0.14684 | 10.94206 | 111.65 |
| 4 | 0.14237 | 0.14873 | 11.94883 | 121.93 |
| 5 | 0.12188 | 0.13415 | 9.78103 | 99.81 |
| 6 | 0.12756 | 0.13047 | 9.78347 | 99.83 |
| 7 | 0.13549 | 0.13841 | 10.45221 | 106.66 |

TABLE 5-9-continued

Solution 00 40° C./75% RH spray content uniformity results

| Sample | Weight Collected, g | Weight Actuated, g | Diazepam Recovered, mg | % Diazepam Recovered |
|---|---|---|---|---|
| 8 | 0.12323 | 0.12543 | 9.41177 | 96.04 |
| 9 | 0.14299 | 0.14517 | 11.35701 | 115.89 |
| Average | 0.13635 | 0.14131 | 10.653 | 108.70 |
| St. Dev. | 0.0097 | 0.0095 | 0.8884 | 9.0649 |
| % RSD | 7.14 | 6.76 | 8.34 | 8.34 |

TABLE 5-10

Solution 02 25° C./60% RH spray content uniformity results

| Sample | Weight Collected, g | Weight Actuated, g | Diazepam Recovered, mg | % Diazepam Recovered |
|---|---|---|---|---|
| 1 | 0.12280 | 0.12611 | 8.88043 | 90.62 |
| 2 | 0.13318 | 0.13549 | 9.55581 | 97.51 |
| 3 | 0.13260 | 0.13452 | 9.71837 | 99.17 |
| 4 | 0.12064 | 0.12305 | 9.48123 | 96.75 |
| 5 | 0.13215 | 0.13582 | 9.34463 | 95.35 |
| 6 | 0.13559 | 0.13790 | 9.48722 | 96.81 |
| 7 | 0.13158 | 0.13371 | 9.43613 | 96.29 |
| 8 | 0.13357 | 0.13495 | 9.79164 | 99.91 |
| 9 | 0.12165 | 0.12443 | 8.84732 | 90.28 |
| Average | 0.12931 | 0.13178 | 9.394 | 95.85 |
| St. Dev. | 0.0058 | 0.0056 | 0.3303 | 3.3701 |
| % RSD | 4.52 | 4.25 | 3.52 | 3.52 |

TABLE 5-11

Solution 02 40° C./75% RH spray content uniformity results

| Sample | Weight Collected, g | Weight Actuated, g | Diazepam Recovered, mg | % Diazepam Recovered |
|---|---|---|---|---|
| 1 | 0.12336 | 0.12563 | 9.02005 | 92.04 |
| 2 | 0.05723 | 0.05792 | 9.43076 | 96.23 |
| 3 | 0.13554 | 0.13908 | 9.93829 | 101.41 |
| 4 | 0.13619 | 0.13679 | 9.87755 | 100.79 |
| 5 | 0.13227 | 0.13414 | 9.64403 | 98.41 |
| 6 | 0.13331 | 0.13515 | 9.80808 | 100.08 |
| 7 | 0.13455 | 0.13844 | 9.31952 | 95.10 |
| 8 | 0.13314 | 0.13736 | 9.28106 | 94.70 |
| 9 | 0.13249 | 0.13387 | 9.32935 | 95.20 |
| Average | 0.12423 | 0.12649 | 9.517 | 97.11 |
| St. Dev. | 0.0254 | 0.0260 | 0.3148 | 3.2119 |
| % RSD | 20.45 | 20.57 | 3.31 | 3.31 |

TABLE 5-12

Suspension 01 25° C./60% RH spray content uniformity results

| Sample | Weight Collected, g | Weight Actuated, g | Diazepam Recovered, mg | % Diazepam Recovered |
|---|---|---|---|---|
| 1 | 0.12873 | 0.12999 | 12.85366 | 91.81 |
| 2 | 0.14011 | 0.14247 | 13.68122 | 97.72 |
| 3 | 0.14515 | 0.14757 | 14.09449 | 100.67 |
| 4 | 0.13205 | 0.13347 | 14.18775 | 101.34 |
| 5 | 0.14554 | 0.14743 | 14.48202 | 103.44 |
| 6 | 0.14473 | 0.14682 | 14.39897 | 102.85 |
| 7 | 0.13229 | 0.13411 | 14.87853 | 106.28 |
| 8 | 0.14357 | 0.14581 | 14.82712 | 105.91 |
| 9 | 0.14741 | 0.14940 | 14.86732 | 106.20 |
| Average | 0.13995 | 0.14190 | 14.252 | 101.80 |
| St. Dev. | 0.0070 | 0.0074 | 0.6602 | 4.7154 |
| % RSD | 5.03 | 5.18 | 4.63 | 4.63 |

TABLE 5-13

Suspension 01 40° C./75% RH spray content uniformity results

| Sample | Weight Collected, g | Weight Actuated, g | Diazepam Recovered, mg | % Diazepam Recovered |
|---|---|---|---|---|
| 1 | 0.14411 | 0.14869 | 13.04770 | 93.20 |
| 2 | 0.14066 | 0.14151 | 13.23277 | 94.52 |
| 3 | 0.13012 | 0.13485 | 13.78126 | 98.44 |
| 4 | 0.14667 | 0.14879 | 13.36970 | 95.50 |
| 5 | 0.14294 | 0.14338 | 12.54309 | 89.59 |
| 6 | 0.13797 | 0.14253 | 13.25396 | 94.67 |
| 7 | 0.13374 | 0.13594 | 13.41984 | 95.86 |
| 8 | 0.12388 | 0.12559 | 14.34944 | 102.50 |
| 9 | 0.13790 | 0.14011 | 13.88564 | 99.18 |
| Average | 0.13755 | 0.14015 | 13.431 | 95.94 |
| St. Dev. | 0.0073 | 0.0073 | 0.5223 | 3.7310 |
| % RSD | 5.28 | 5.19 | 3.89 | 3.89 |

TABLE 5-14

Suspension 03 25° C./60% RH spray content uniformity results

| Sample | Weight Collected, g | Weight Actuated, g | Diazepam Recovered, mg | % Disazepam Recovered |
|---|---|---|---|---|
| 1 | 0.13604 | 0.13897 | 25.93418 | 92.62 |
| 2 | 0.14608 | 0.14792 | 26.21721 | 93.63 |
| 3 | 0.15294 | 0.15425 | 30.05570 | 107.34 |
| 4 | 0.14728 | 0.14910 | 25.78804 | 92.10 |
| 5 | 0.15352 | 0.15493 | 26.60721 | 95.03 |
| 6 | 0.15242 | 0.15401 | 29.51030 | 105.39 |
| 7 | 0.15118 | 0.15254 | 28.43104 | 101.54 |

TABLE 5-14-continued

Suspension 03 25° C./60% RH spray content uniformity results

| Sample | Weight Collected, g | Weight Actuated, g | Diazepam Recovered, mg | % Disazepam Recovered |
|---|---|---|---|---|
| 8 | 0.15322 | 0.15556 | 28.03664 | 100.13 |
| 9 | 0.15197 | 0.15393 | 26.82906 | 95.82 |
| Average | 0.14941 | 0.15125 | 27.490 | 98.18 |
| St. Dev. | 0.0057 | 0.0053 | 1.5812 | 5.6472 |
| % RSD | 3.79 | 3.50 | 5.75 | 5.75 |

TABLE 5-15

Suspension 03 40° C./75% RH spray content uniformity results

| Sample | Weight Collected, g | Weight Actuated, g | Diazepam Recovered, mg | % Disazepam Recovered |
|---|---|---|---|---|
| 1 | 0.13574 | 0.13797 | 28.14588 | 100.52 |
| 2 | 0.13639 | 0.13803 | 27.04437 | 96.59 |
| 3 | 0.14082 | 0.14195 | 26.78985 | 95.68 |
| 4 | 0.12962 | 0.13249 | 29.07192 | 103.83 |
| 5 | 0.12518 | 0.12683 | 27.39785 | 97.85 |
| 6 | 0.14423 | 0.14541 | 28.50133 | 101.79 |
| 7 | 0.13922 | 0.14096 | 27.34617 | 97.66 |
| 8 | 0.14146 | 0.14313 | 27.17415 | 97.05 |
| 9 | 0.14902 | 0.15344 | 27.20939 | 97.18 |
| Average | 0.13796 | 0.14002 | 27.631 | 98.68 |
| St. Dev. | 0.0073 | 0.0076 | 0.7642 | 2.7294 |
| % RSD | 5.28 | 5.43 | 2.77 | 2.77 |

Example 6

All of the solutions and suspensions described in Examples 3 and 4 are formulated as described in Examples 3 and 4, with the addition of a suitable amount of an alkyl glycoside, as described herein, such as dodecyl maltoside, tetradecyl maltoside, sucrose dodecanoate, sucrose monostearate, sucrose distearate, and/or combinations of two or more thereof, or marketed as Intravail® by Aegis Therapeutics, San Diego, Calif. The solutions and suspensions with added alkyl glycoside may then be put up on stability as described in Example 5, mutatis mutandis.

Example 7

The solutions and suspensions of Examples 3, 4 and 6 are evaluated for pharmacokinetics in a suitable animal model, such as in mice, rats, rabbits or dogs. First each animal (e.g. rabbit) is administered an amount of a benzodiazepine drug intravenously. The amount of intravenously dosed benzodiazepine drug is selected to be less, e.g. roughly half, of what is considered an effective dose administered nasally. For example, the intravenous dose of diazepam administered to rabbits is about 0.05 to about 0.2 mg/kg, e.g. about 0.1 mg/kg. Blood is collected immediately before administration and at specific time points post-administration. Plasma blood levels of the drug are assayed for each of the blood samples. After at least a one day washout period, each animal is administered, intranasally, an amount of a solution or suspension as described in Examples 3, 4 and 6. Blood is collected immediately before administration and at substantially the same specific time points as the IV dose post-administration. Pharmacokinetic curves (blood plasma concentration of drug versus time) are constructed for the intravenous route of administration and for each of the solutions and suspensions administered by the intranasal administration route.

Toxicity is assessed by known means. In particular, histological samples are collected from the nasal mucosal tissues of the test animals. Other toxological methods are optionally employed as well.

Example 8

The solutions and suspensions of Examples 3, 4 and 6 are evaluated for their ability to deliver drug across the blood brain barrier in a suitable animal model, such as in mice, rats, rabbits or dogs. Each animal is administered, intranasally, an amount of a solution or suspension as described in Examples 3, 4 and 6, with the solution or suspension optionally containing an imaging agent, such as a dye, that may be used as a proxy for determining the ability of the drug to cross the blood brain barrier. The drug or imaging agent is detected at selected time points after administration of the suspension or solution to determine how well the drug or imaging agent crosses the blood brain barrier. These results may be compared with analogous result obtained with an intravenous solution containing the drug or imaging agent.

Example 9

The above-described solutions and/or suspensions can be evaluated for pharmacokinetics in humans. Normal, healthy human test subjects are administered an amount of the drug intravenously. The amount chosen for intravenous administration may be any amount, but is conveniently a dose that is considered effective in treating seizure in humans. For example, an IV dose of diazepam administered to humans may be in the range of 1 to 15 mg, e.g. about 7.5 mg. Blood is collected immediately before administration and at selected time points after administration. Plasma blood levels of the drug are assayed for each of the blood samples. After at least a one day washout period, each subject is administered, intranasally, an amount of a solution or suspension as described herein. Blood is collected immediately before administration and at substantially the same time points after administration as the intravenous time points. Pharmacokinetic curves (blood plasma concentration of drug versus time) are constructed for the intravenous and intranasal administration routes.

Example 10

The above-described solutions and/or suspensions can be evaluated for efficacy in a suitable animal model. Briefly, for each dose of suspension or solution to be tested, a test animal is stimulated with a seizure inducing stimulus. The stimulus may be light, sound, chemical or other stimulus effective to induce seizure in the model animal. Once the animal has begun to seize, a solution or suspension as described herein is administered intranasally to the animal. The efficacy of the dose of the solution and/or suspension is evaluated based upon the animal's response to the test dose. This procedure is repeated through sufficient iterations, and at sufficient numbers of doses, to identify a dose that is considered effective to treat seizure by intranasal administration of the drug.

Example 11

A pharmaceutical composition comprising diazepam was prepared as a composition formulated as a solution to be delivered via a nasal delivery device. The solution was prepared according to the procedure outlined in the flow diagram of FIG. 4. The ingredients used in the 100 mg/mL diazepam solution are set forth in Table 11-1, below:

TABLE 11-1

| Ingredient | Concentration (% (w/v)) |
|---|---|
| Diazepam | 10.00% (w/v) |
| α-tocopherol* | 56.47% (w/v) |
| Ethanol (dehydrated) | q.s. ((~18.07) % (w/v)) |
| Intravail A3** | 0.25% (w/v) |
| Benzyl alcohol | 10.50% (w/v) |

*Vitamin E,
**Dodecyl maltoside

A batch of solution of Table 11-1 was prepared and subjected to stability testing at 25° C./60% R.H. for 12 months. The following table provides stability determinations for this batch at initial, 3 month, 6 month and 12 month time points.

| Test Parameter | Initial % Label Claim (100 mg/mL) | 1 Month | 3 Month | 6 Month |
|---|---|---|---|---|
| Appearance | Pale amber to amber solution | Amber solution | Amber solution | Amber solution |
| Diazepam % Label Claim | 103.3 | 99.5 | 99.2 | 99.1 |

A batch of solution of Table 11-1 was prepared and subjected to stability testing at 30° C./65% R.H. (accelerated conditions) for 12 months. The following table provides stability determinations for this batch at initial, 1 month and 12 month time points.

| Test Parameter | Initial % Label Claim (100 mg/mL) | 1 Month | 6 Month |
|---|---|---|---|
| Appearance | Pale amber to amber solution | Amber solution | Amber solution |
| Diazepam % Label Claim | 103.3 | 97.8 | 99.7 |

A batch of solution of Table 11-1 was prepared and subjected to stability testing at 40° C./75% R.H. (accelerated conditions) for 12 months. The following table provides stability determinations for this batch at initial, 3 month, 6 month and 12 month time points.

| Test Parameter | Initial % Label Claim (100 mg/mL) | 1 Month | 3 Month | 6 Month |
|---|---|---|---|---|
| Appearance | Pale amber to amber solution | Amber solution | Amber solution | Amber solution |
| Diazepam % Label Claim | 103.3 | 97.9 | 100.0 | 99.4 |

The suspension formulation is set forth in Table 11-2, below

| Component | Function | Concentration (mg/mL) |
|---|---|---|
| Diazepam | Active | 100.0 |
| Methyl Paraben | Preservative | 2.0 |
| Propyl Paraben | Preservative | 0.5 |
| Intravail A3 | Absorption aid | 2.5 |
| Vitamin E TPGS | Dispersant | 10.0 |
| Propylene Glycol | Dispersant | 100.0 |

-continued

| Component | Function | Concentration (mg/mL) |
|---|---|---|
| Povidone | Suspending agent | 5.0 |
| Water | Carrier | q.s. to 1.0 mL |

A batch of suspension of Table 11-2 was prepared and subjected to stability testing at 25° C./60% R.H. for 3 months. The following table provides stability determinations for this batch at initial and 3 month time points.

| Test Parameter | Initial % Label Claim (100 mg/mL) | 3 Month |
|---|---|---|
| Appearance | Opaque white liquid | Opaque white liquid |
| Diazepam % Label Claim | 104.4 | 102.1 |

A batch of suspension of Table 11-2 was prepared and subjected to stability testing at 30° C./65% R.H. (accelerated conditions) for 1 month. The following table provides stability determinations for this batch at initial and 1 month time points.

| Test Parameter | Initial % Label Claim (100 mg/mL) | 1 Month |
|---|---|---|
| Appearance | Opaque white liquid | Opaque white liquid |
| Diazepam % Label Claim | 104.4 | 102.9 |

A batch of suspension of Table 11-2 was prepared and subjected to stability testing at 40° C./75% R.H. (accelerated conditions) for 3 months. The following table provides stability determinations for this batch at initial, 1 month and 3 month time points.

| Test Parameter | Initial % Label Claim (100 mg/mL) | 1 Month | 3 Month |
|---|---|---|---|
| Appearance | Opaque white liquid | Opaque white liquid | White liquid |
| Diazepam % Label Claim | 104.4 | 102.7 | 108.7 |

A three-period, three-treatment, six-sequence, randomized cross-over study was conducted in healthy volunteers. For each dose, each volunteer was domiciled for at least 12 hours prior to each dose and until after a 24 hour pharmacokinetic sample was collected. Single doses of 100 µL of the pharmaceutical compositions described in Tables 11-1 and 11-2 were administered to each volunteer as one spray to the left nostril of 100 µL per spray. Pharmacokinetic samples were collected at 22 time points over 10 days. (PK time points: 2.5, 5, 10, 15, 20, 30 and 45 minutes, 1, 1.5, 2, 4, 12, 24, 36, 48, 72, 96, 144, 192 and 240 hours after each dose.) No serious adverse events were noted. PK data were compared with those obtained with 5 mg of diazepam administered intravenously. The PK data are summarized in Table 11-3 and FIGS. 1-3.

The solution of Table 11-1 and the suspension of Table 11-2 were found to be well-tolerated with only mild adverse events reported. The solution of Table 11-1 was further found to have similar bioavailability to intravenous administration of diazepam (96% of i.v.) The intranasal formulation of Table 11-1 exhibited a Tmax of 1.5 hours, a Cmax of approximately 272 ng/mL. These results are comparable to those reported in the literature for commercially available diazepam gel (Diastat®).

Solutions similar to those set forth in Table 11-1 can be prepared consisting of: diazepam (5-15% (w/v)), dodecyl maltoside (0.01-1% (w/v)), vitamin E (45-65% (w/v)), ethanol (10-25% (w/v)) and benzyl alcohol (5-15% (w/v)); diazepam (9-11% (w/v)), dodecyl maltoside (0.1-0.5% (w/v)), vitamin E (50-60% (w/v)), ethanol (15-22.5% (w/v)) and benzyl alcohol (7.5-12.5% (w/v)); or diazepam (10% (w/v)), dodecyl maltoside (0.15-0.3% (w/v)), vitamin E (50-60% (w/v)), ethanol (17-20% (w/v)) and benzyl alcohol (10-12% (w/v)).

Solutions similar to those set forth in Table 11-1 achieve bioavailability that is from about 80-125% of that achieved with the same benzodiazepine administered intravenously, e.g. bioavailability that is from about 90-110% of that achieved with the same benzodiazepine administered intravenously or about 92.5 to 107.5% that obtained with the same benzodiazepine administered intravenously. Such solutions may be used in methods of treating a patient with a disorder which may be treatable with a benzodiazepine drug, such as seizure, epileptic seizure and/or breakthrough seizure. In some embodiments, solutions described herein may be used to treat a disorder such as is treated with Diastat® diazepam gel.

A summary of pharmacokinetic data obtained for the solution and a suspension form of diazepam is shown below in Table 11-3:

TABLE 11-3

Summary of Pharmacokinetic Parameters for Intranasal (10 mg) and IV (5 mg) Diazepam

| | Diazepam Nasal Spray (10 mg/100 µL) | | | | Diazepam Injection | |
|---|---|---|---|---|---|---|
| | NRL-1.A Suspension | | NRL-1.B Solution | | 5 mg/mL IV | |
| Parameter[a] | n | Mean (SD)[b] | n | Mean (SD)[b] | n | Mean (SD)[b] |
| $C_{max}$ (ng/mL) | 24 | 221 (78.6) | 24 | 272 (100) | 24 | 555 (316) |
| $T_{max}$ (h)[b] | 24 | 1.00 (0.6, 2.0) | 24 | 1.50 (0.8, 4.0) | 24 | 0.03 (0.03, 0.50) |
| $AUC_{0-t}$ (h × ng/mL) | 24 | 5229 (1463) | 24 | 7340 (1882) | 24 | 3832 (1150) |
| $AUC_{0-\infty}$ (h × ng/mL) | 20 | 5381 (1409) | 20 | 7338 (2072) | 24 | 4104 (1318) |
| $\lambda z$ (h$^{-1}$) | 20 | 0.0142 (0.0053) | 20 | 0.0155 (0.0046) | 24 | 0.0142 (0.0055) |
| t½ (h) | 20 | 56.2 (23.0) | 20 | 49.2 (16.9) | 24 | 56.2 (21.0) |

Figure 2:
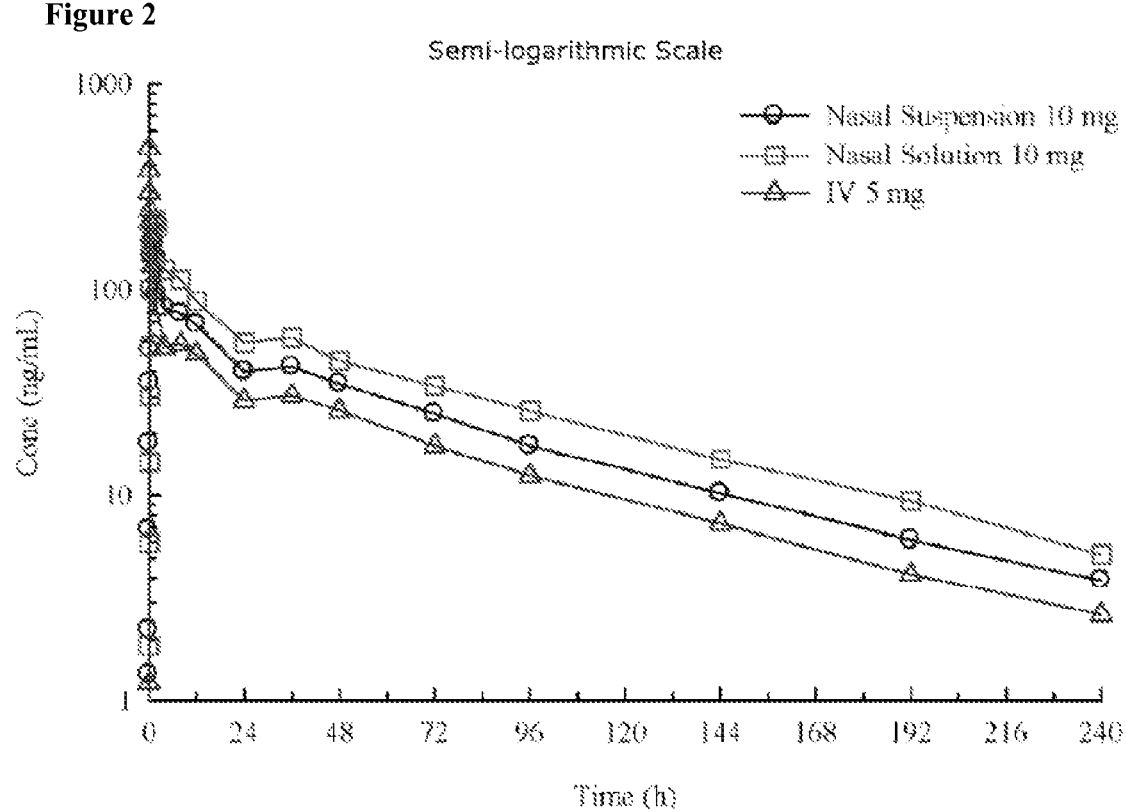
FIG. 2 depicts a 240 hour semi-logarithmic plot of the arithmetic mean plasma concentration of diazepam after intranasal administration of 10 mg of diazepam as a suspension of Table 11-2, intranasal administration 10 mg of diazepam as a solution of Table 11-1, and 5 mg of diazepam as an intravenous injection.
Figure 3:
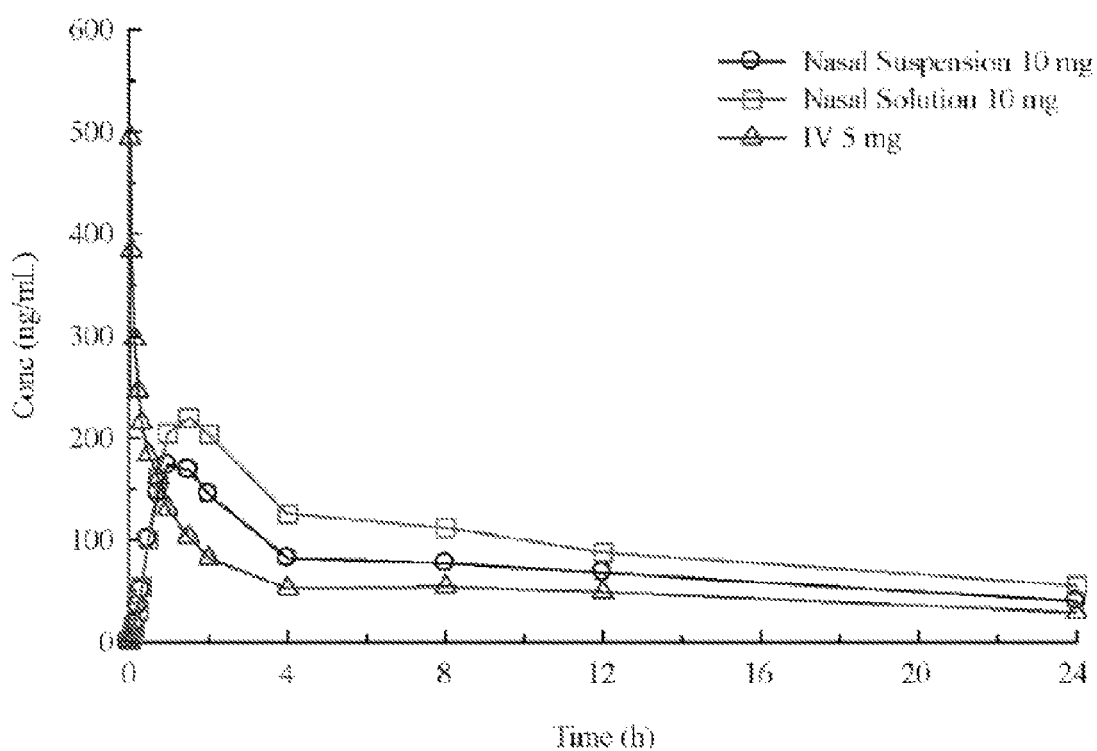
FIG. 3 depicts a 24 hour linear plot of the arithmetic mean plasma concentration of diazepam after intranasal administration of 10 mg of diazepam as a suspension of Table 11-2, intranasal administration 10 mg of diazepam as a solution of Table 11-1, and 5 mg of diazepam as an intravenous injection.

[a]Mean values are presented as arithmetic means.
[b]Median (min, max) reported for $T_{max}$ The data collected in the study are further illustrated in FIGS. 1-3. FIG. 1 is a linear scale plot of the arithmetic mean of the plasma concentration of diazepam after intranasal (IN) administration of 10 mg of diazepam as the suspension of Table 11-2 and after IN administration of 10 mg of diazepam as a solution of Table 11-1 compared to intravenous (IV) administration of 5 mg of diazepam. FIG. 2 is a semi-logarithmic scale plot of the same data shown in FIG. 1. FIG. 3 shows the first 24 hours of data from FIG. 1 on a linear scale.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical solution for nasal administration consisting of:
   (a) a benzodiazepine drug;
   (b) one or more natural or synthetic tocopherols or tocotrienols, or any combinations thereof, in an amount from about 30% to about 95% (w/w);
   (c) ethanol and benzyl alcohol in a combined amount from about 10% to about 70% (w/w); and
   (d) an alkyl glycoside.

2. The pharmaceutical solution of claim 1, wherein the benzodiazepine drug is selected from the group consisting of: alprazolam, brotizolam, chlordiazepoxide, clobazam, clonazepam, clorazepam, demoxazepam, diazepam, flumazenil, flurazepam, halazepam, midazolam, nordazepam, medazepam, nitrazepam, oxazepam, lorazepam, prazepam, quazepam, triazolam, temazepam, loprazolam, any pharmaceutically-acceptable salts thereof, and any combinations thereof.

3. The pharmaceutical solution of claim 2, wherein the benzodiazepine drug is diazepam, or a pharmaceutically-acceptable salt thereof.

4. The pharmaceutical solution of claim 1, wherein said benzodiazepine is present in the pharmaceutical solution in a concentration from about 1 to about 20% (w/v).

5. The pharmaceutical solution of claim 4, wherein said benzodiazepine is diazepam.

6. The pharmaceutical solution of claim 1, wherein the one or more natural or synthetic tocopherols or tocotrienols are selected from the group consisting of: α-tocopherol, β-tocopherol, γ-tocopherol, δ-tocopherol, α-tocotrienol, β-tocotrienol, γ-tocotrienol, δ-tocotrienol, tocophersolan, any isomers thereof, any esters thereof, any analogs or derivatives thereof, and any combinations thereof.

7. The pharmaceutical solution of claim 1, wherein the ethanol is present in the pharmaceutical solution in a concentration of from 1 to 25% (w/v) and the benzyl alcohol is present in the pharmaceutical solution in a concentration from 1 to 25% (w/v).

8. The pharmaceutical solution of claim 1, wherein the ethanol is present in the solution in a concentration of from 10 to 22.5% (w/v) and the benzyl alcohol is present in the solution in a concentration of from 7.5 to 12.5% (w/v).

9. The pharmaceutical solution of claim 8, wherein the benzodiazepine is present in the pharmaceutical solution in a concentration from about 20 mg/mL to about 200 mg/mL.

10. The pharmaceutical solution of claim 1, wherein the one or more natural or synthetic tocopherols or tocotrienols, or any combinations thereof, is in an amount from about 45% to about 85% (w/w).

11. The pharmaceutical solution of claim 10, wherein the one or more natural or synthetic tocopherols or tocotrienols, or any combinations thereof, is in an amount from about 50% to about 75% (w/w).

12. The pharmaceutical solution of claim 1, wherein the ethanol and benzyl alcohol are present in the pharmaceutical solution in a combined amount from about 15% to about 55% (w/w).

13. The pharmaceutical solution of claim 12, wherein the ethanol and benzyl alcohol are present in the pharmaceutical solution in a combined amount from about 25% to about 40% (w/w).

14. The pharmaceutical solution of claim 1, consisting of 5-15% (w/v) diazepam, 0.01-1% (w/v) alkyl glycoside, 45-65% (w/v) vitamin E, 10-25% (w/v) ethanol and 5-15% (w/v) benzyl alcohol.

15. The pharmaceutical solution of claim 1, wherein the alkyl glycoside is present in pharmaceutical solution in a concentration of at least about 0.01% (w/w).

16. The pharmaceutical solution of claim 15, wherein the alkyl glycoside is present in the pharmaceutical solution in an amount of 0.01% to 1% (w/w).

17. The solution of claim 1, consisting of diazepam, vitamin E, ethanol, benzyl alcohol and dodecyl maltoside.

18. The solution of claim 17, consisting of about 56.47% (w/v) vitamin E, about 10.5% (w/v) benzyl alcohol, about 10% (w/v) diazepam, about 0.25% (w/v) dodecyl maltoside, q.s. dehydrated ethanol.

19. The pharmaceutical solution of claim 14, consisting of 5-15% (w/v) diazepam, 0.01-1% (w/v) dodecyl maltoside, 45-65% (w/v) vitamin E, 10-25% (w/v) ethanol and 5-15% (w/v) benzyl alcohol.

20. The pharmaceutical solution of claim 14, consisting of 9-11% (w/v) diazepam, 0.1-0.5% (w/v) dodecyl maltoside, 50-60% (w/v) vitamin E, 15-22.5% (w/v) ethanol and 7.5-12.5 (w/v) benzyl alcohol.

21. The pharmaceutical solution of claim 14, consisting of 10% (w/v) diazepam, 0.15-0.3% (w/v) dodecyl maltoside, 50-60 (w/v) vitamin E, 17-20% (w/v) ethanol and 10-12% (w/v) benzyl alcohol.

22. The solution of claim 16, wherein the alkyl glycoside is dodecyl maltoside.

* * * * *